US009170221B2

(12) United States Patent
Heider

(10) Patent No.: US 9,170,221 B2
(45) Date of Patent: Oct. 27, 2015

(54) NMR CRYSTALLOGRAPHY METHODS FOR THREE-DIMENSIONAL STRUCTURE DETERMINATION

(76) Inventor: Elizabeth M. Heider, South Jordan, UT (US)

(*) Notice: Subject to any disclaimer, the term of this patent is extended or adjusted under 35 U.S.C. 154(b) by 831 days.

(21) Appl. No.: 13/248,815

(22) Filed: Sep. 29, 2011

(65) Prior Publication Data

US 2013/0328558 A1    Dec. 12, 2013

Related U.S. Application Data

(60) Provisional application No. 61/389,158, filed on Oct. 1, 2010.

(51) Int. Cl.
| | |
|---|---|
| G01R 33/483 | (2006.01) |
| G01R 33/485 | (2006.01) |
| G01R 33/34 | (2006.01) |
| G01N 24/08 | (2006.01) |

(52) U.S. Cl.
CPC .................................... G01N 24/087 (2013.01)

(58) Field of Classification Search
CPC ..... G01R 33/34; G01R 33/483; G01R 33/485; G01R 33/465; G01N 24/087; G01N 24/08; G06F 19/16; G06F 19/18
USPC ........... 324/300–322; 702/19, 21; 703/11, 12; 436/173
See application file for complete search history.

(56) References Cited

U.S. PATENT DOCUMENTS

| | | | |
|---|---|---|---|
| 6,027,941 A * | 2/2000 | Jarvie et al. | ................... 436/173 |
| 2002/0041850 A1 | 4/2002 | Szyperski | |
| 2004/0038216 A1 | 2/2004 | Hajduk et al. | |

FOREIGN PATENT DOCUMENTS

WO    WO 00/72004 A2    11/2000

OTHER PUBLICATIONS

Salager, Elodie, et al. "Powder NMR crystallography of thymol." Feb. 25, 2009; Physical Chemistry Chemical Physics 11.15 (2009): 2610-2621.*
International Search Report and Written Opinion for International Application No. PCT/US 2013/069847, mailed Sep. 4, 2014.*
Alderman, D.W., et al., "A sensititve, high resolution magic angle turning experiment for measuraing chemical shift tensor principal values," *Mol. Phys.* 95(6):1113-1126, Taylor & Francis Ltd., United Kingdon (1998).
Alderman D.W., et al., "Comparing, Modeling, and Assigning Chemical-Shift Tensors in the Cartesian, Irreducible Spherical, and Icosahedral Representations," *J. Magn. Reson. Ser. A.* 101:188-197, Academic Press, Inc., United States (1993).
Asmadi, A., et a., "Revisiting the Blind Tests in Crystal Structure Prediction: Accurate Energy Ranking of Molecular Crystals," *J. Phys. Chem. B* 113:16303-16313, American Chemical Society, United States (2009).

(Continued)

*Primary Examiner* — Melissa Koval
*Assistant Examiner* — Rishi Patel
(74) *Attorney, Agent, or Firm* — Sterne, Kessler, Goldstein & Fox P.L.L.C.

(57) ABSTRACT

The invention relates to new uses of nuclear magnetic resonance (NMR) crystallography methods to determine and/or characterize the three-dimensional structure of compounds of interest.

14 Claims, 5 Drawing Sheets

(56) References Cited

OTHER PUBLICATIONS

Figure 1:
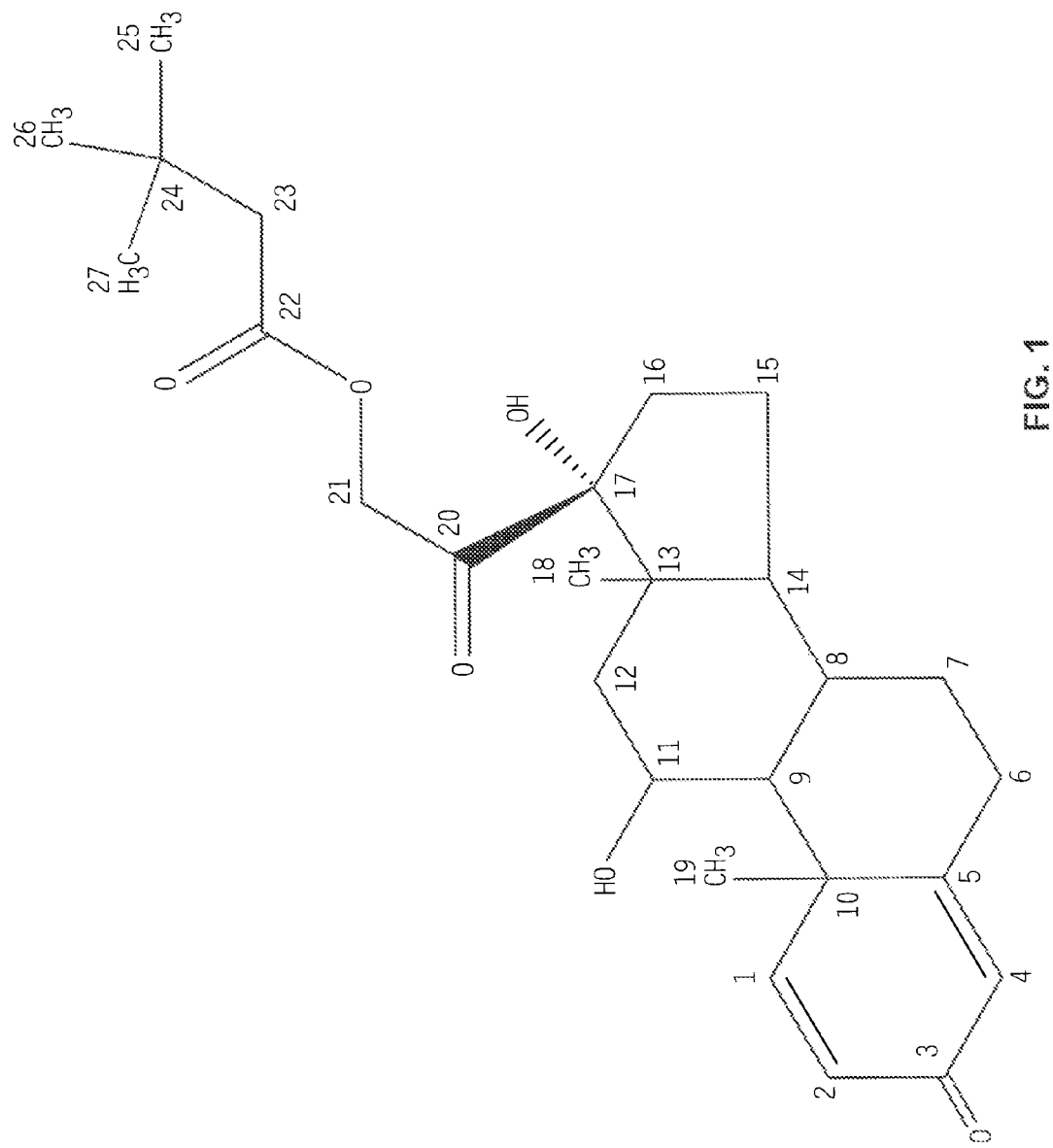

Day, G.M. and Motherwell, S., "The 2004 Blind Test of Crystal Structure," *Acta. Cryst.* A60:s63, 22nd European Crystallographic Meeting, Budapest, Aug. 26, 31, United Kingdon (2004).

de Dios, A.C. and Oldfield, E., "Methods for computing nuclear magnetic resonance chemical shielding in large system. Multiple cluster and charge field approaches," *Chemcial Physics Letters* 205(1):108-116, Elsevier Science Publishers B.V., Netherlands (1993).

de Dios, A.C., et al., "Predicting Carbon-13 Nuclear Magnetic Resonance Chemical Shielding Tensors in Zwitterionic L-Threonine and L-Tyrosine via Quantum Chemistry," *J. Am. Chem. Soc.* 116:7784-786, the American Chemical Society, United States (1994).

Etter, M.C., "Encoding and Decoding Hydrogen-Bond Patterns of Organic Compounds," *Acc. Chem. Res.* 23(4):120-126, American Chemcial Society, United States (1990).

Goho, A., "Tricky Business: The crystal form of a drug can be the secret to its success," *Science News* 166:122-124, Science Service, United States (2004).

Harper, J.K., et al., "Sterochemical Analysis by Solid-State NMR: Structural Predictions in Ambuic Acid," *J. Org. Chem.* 68(12):4609-4614, American Chemical Society, United States (2003).

Heider, E.M., et al., "Structural characterization of an anhydrous polymorph of paclitaxel by solid-state NMR," *Phys. Chem. Chem. Phys.* 9:6082-6097, Royal Society of Chemistry, United States (2007).

Jeffrey, G.A., "Hydrogen-Bonding: An Update," *Crystall. Rev.* 9(2-3):135-176, Taylor & Francis Ltd., United Kingdom (2003).

Lommerse, J.P.M., et al., "A test of crystal structure prediction of small organic molecules," *Acta Cryst.* B56:647-661, International Union of Crystallography, Great Britain (2000).

Motherwell, W.D.S., et al., "Crystal structure prediction of small organic molecules: a second blind test," *Acta Cryst.* B58:647-661, International Union of Crystallography, Great Britain (2002).

Newsam, J.M., et al., "Crystal structure solution and prediction via global and local optimization," *Curr. Opin. Solid State Mat. Sci.* 4:515-528, Elsevier Science Ltd., Great Britain (1999).

Price, S.L., "The computational prediction of pharmaceutical crystal structures and polymorphism," *Adv. Drug Deliv. Rev.* 56:301-319, Elsevier B.V., Netherlands (2004).

Rienstra, C.M., et al., "De novo determination of peptide structure with solid-state magic-angle spinning NMR spectroscopy," *Proc. Natl. Acad. Sci. USA* 99(16):10260-10265, National Academy of Sciences, United States (2002).

Stueber, D., et al., "The calculation of $^{13}$C chemical shielding tensors in ionic compounds utilizing point charge arrays obtained from Ewald lattice sums," *The J. Chem. Phys.* 114(21):9236-9243, American Institute of Physics, United States (2001).

Alderman, D.W., et al., "A sensitive, high resolution magic angle turning experiment for measuring chemical shift tensor principal values," *Mol Phys* 95(6):1113-1126, Taylor & Francis Ltd., England (1998).

Allen, F.H., "The Cambridge Structural Database: a quarter of a million crystal structures and rising," *Acta Crystallographica* B58:380-388, International Union of Crystallography, England (2002).

Baias, M., et al., "De Novo Determination of the Crystal Structure of a Large Drug Molecule by Crystal Structure Prediction-Based Powder NMR Crystallography," *J Am Chem Soc* 135:17501-17507, American Chemical Society, United States (Oct. 2013).

Brouwer, D.H., et al., "NMR crystallography of *p-tert*-butylcalix[4]arene host-guest complexes using $^1$H complexation-induced chemical shifts," *Phys Chem Chem Phys* 10(26):3857-3860, The Royal Society of Chemistry, England (2008).

Byrn, S.R., et al., "Solid-State Pharmaceutical Chemistry," *Chem Mater* 6:1148-1158, American Chemical Society, United States (1994).

Carignani, E., et al., "$^{13}$C Chemical Shielding Tensors: A Combined Solid-State NMR and DFT Study of the Role of Small-Amplitude Motions," *J Phys Chem C* 115:25023-25029, American Chemical Society, United States (Nov. 2011).

Castellani, F., et al., "Structure of a protein determined by solid-state magic-angle-spinning NMR spectroscopy," *Nature* 420:98-102, Nature Publishing Group, England (2002).

Czernek, J., et al., "The comparison of approaches to the solid-state NMR-based structural refinement of vitamin $B_1$ hydrochloride and of its monohydrate," *Chemical Physics Letters* 555:135-140, Elsevier B.V., Netherlands (Nov. 2012).

Dudenko, D.V., et al., "An NMR crystallography DFT-D approach to analyse the role of intermolecular hydrogen bonding and π-π interactions in driving cocrystallisation of indomethacin and nicotinamide," *CrystEngComm* 15:8797-8807, The Royal Society of Chemistry, England (Aug. 2013).

Franks, W.T., et al., "Dipole tensor-based atomic-resolution structure determination of a nanocrystalline protein by solid-state NMR," *Proc Natl Acad Sci* 105(12):4621-4626, National Academy of Sciences, United States (2008).

Griffin, J.M., et al., "High-Resolution $^{19}$F MAS NMR Spectroscopy: Structural Disorder and Unusual *J* Couplings in a Fluorinated Hydroxy-Silicate," *J Am Chem Soc* 132:15651-15660, American Chemical Society, United States (Oct. 2010).

Halling, M.D., et al., "Solid-State $^{13}$C NMR Investigations of Cyclophanes: [2.2] Paracyclophane and 1,8,-Dioxa[8](2,7)pyrenophane," *J Phys Chem A* 116:5193-5198, American Chemical Society, United States (Apr. 2012).

Harper, J.K., et al., "Solid-State $^{13}$C Chemical Shift Tensors in Terpenes. 2. NMR Characterization of Distinct Molecules in the Asymmetric Unit and Steric Influences on Shift in Parthenolide," *J Am Chem Soc* 121:6488-6496, American Chemical Society, United States (1999).

Harper, J.K. and Grant, D.M., "Solid-State $^{13}$C Chemical Shift Tensors in Terpenes. 3. Structural Characterization of Polymorphous Verbenol," *J Am Chem Soc* 122:3708-3714, American Chemical Society, United States (2000).

Harper, J.K., et al.,"Terrein," *Acta Crystallographica* C56:e570-e571, International Union of Crystallography, England (2000).

Harper, J.K., et al., "Characterization of Stereochemistry and Molecular Conformation Using Solid-State NMR Tensors," *J Am Chem Soc* 123:9837-9842, American Chemical Society, United States (2001).

Harper, J.K., et al., "$^{13}$C NMR Investigation of Solid-State Polymorphism in 10-Deacetyl Baccatin III," *J Am Chem Soc* 124:10589-10595, American Chemical Society, United States (2002).

Harper, J.K., et al., "Stereochemical Analysis by Solid-State NMR: Structural Predictions in Ambuic Acid," *J Org Chem* 68:4609-4614, American Chemical Society, United States (2003).

Harper, J.K., et al., "A Combined Solid-State NMR and X-ray Powder Diffraction Study of a Stable Polymorph of Paclitaxel," *Crystal Growth & Design* 5(5):1737-1742, American Chemical Society, United States (2005).

Harper, J.K. And Grant, D.M., "Enhancing Crystal-Structure Prediction with NMR Tensor Data," *Crystal Growth & Design* 6(10):2315-2321, American Chemical Society, United States (2006).

Harper, J.K., et al., "Characterizing Challenging Microcrystalline Solids with Solid-State NMR Shift Tensor and Synchrotron X-ray Powder Diffraction Data: Structural Analysis of Ambuic Acid," *J Am Chem Soc*128:1547-1552, American Chemical Society (2006).

Harper, J.K., et al., "Pursuing structure in microcrystalline solids with independent molecules in the unit cell using $^1$H-$^{13}$C correlation data," *J Magn Reson* 189(1):20:1-28, Wiley-Liss, United States (2007).

Harper, J.K., "Chemical Shift Anisotropy & Asymmetry: Relationships to Crystal Structure," in *NMR Crystallography*, Harris, R.K., ed., pp. 113-124, John Wiley & Sons, Ltd., England (2009).

Harper, J.K., et al., "A Combined Solid-State NMR and Synchrotron X-ray Diffraction Powder Study on the Structure of the Antioxidant (+)-Catechin 4.5-hydrate" *J Am Chem Soc* 132:2928-2937, American Chemical Society, United States (Feb. 2010).

(56) References Cited

OTHER PUBLICATIONS

Harper, J.K., et al., "Refining crystal structures with experimental $^{13}$C NMR shift tensors and lattice-including electronic structure methods," *CrystEngComm 15*:8693-8704, The Royal Society of Chemistry, England (May 2013).

Harper, J.K. and Iuliucci, R.J., "C-13 Chemical-Shift Tensors in Organic Materials," *Encyclopedia of Analytical Chemistry*, 38 pages, John Wiley & Sons, Ltd., United States (2014).

Harris, R.K., "NMR studies of organic polymorphs & solvates," *Analyst 131*:351-373, The Royal Society of Chemistry, England (2006).

Heider, E.M., et al., "Structural characterization of an anhydrous polymorph of paclitaxel by solid-state NMR," *Phys Chem Chem Phys 9*(46):6083-6097, The Royal Society of Chemistry, England (2007).

Hong, M., et al., "Site-Resolved Determination of Peptide Torsion angle φ from the Relative Orientations of Backbone N—H and C—H Bonds by Solid State NMR," *J Phys Chem B 101*:5869-5874, American Chemical Society, United States (1997).

Jaworska, M., et al., "NMR Crystallography Comparative Studies of Chiral (1R,2S,3R,5R)-3-Amino-6,6-dimethylbicyclo[3.1.1]heptan-2-ol and Its p-Toluenesulfonamide Derivative," *Crystal Growth & Design 12*:5956-5965, American Chemical Society, United States (Nov. 2012).

Kalakewich, K., et al., "Establishing Accurate High-Resolution Crystal Structures in the Absence of Diffraction Data and Single Crystals—An NMR Approach," *Crystal Growth & Design 13*:5391-5396, American Chemical Society, United States (Nov. 2013).

Lai, J., et al., "X-ray and NMR Crystallography in an Enzyme Active Site: The Indoline Quinonoid Intermediate in Tryptophan Synthase," *J Am Chem Soc 133*(1):4-7, American Chemical Society, United States (Dec. 2010).

Liu, W., et al., "Influence of Structure on the Spectroscopic Properties of the Polymorphs of Piroxicam," *J Phys Chem B 114*(49):16641-16649, American Chemical Society, United States (Nov. 2010).

Markwick, P.R.L., et al., "Structural Biology by NMR: Structure, Dynamics, and Interactions," *PLoS Computational Biology 4*(9):e1000168:1-7, Public Library of Science, United States (2008).

McDermott, A.E., "Structural and dynamic studies of proteins by solid-state NMR spectroscopy: rapid movement forward," *Current Opinion in Structural Biology* 14:554-561, Elsevier Ltd., England (2004).

Montelione, G.T., et al., "Protein NMR spectroscopy in structural genomics," *Nature Structural Biology 7*(Suppl):982-985, Nature America Inc., United States (2000).

Mukkamala, D., et al., "A Solid State $^{13}$3C NMR, Crystallographic, and Quantum Chemical Investigation of Phenylalanine and Tyrosine Residues in Dipeptides and Proteins," *J Am Chem Soc 129*:7385-7392, American Chemical Society, United States (2007).

Pawlak, T., et al., "NMR crystallography of α-poly(L-lactide)," *Phys Chem Chem Phys 15*:3137-3145, The Royal Society of Chemistry, England (Dec. 2012).

Pawlak, T., and Potrzebowski, M.J., "Fine Refinement of Solid-State Molecular Structures of Leu- and Met- Enkephalins by NMR Crystallography," *J Phys Chem B 118*:3298-3309, American Chemical Society, United States (Mar. 2014).

Rienstra, C.M., et al., "De novo determination of peptide structure with solid-state magic-angle spinning NMR spectroscopy," *Proc Natl Acad Sci USA 99*(16):10260-10265, National Academy of Sciences, United States (2002).

Salager, E., et al., "Powder NMR crystallography of thymol," *Phys Chem Chem Phys 11*(15):2610-2621, The Royal Society of Chemistry, England (Feb. 2009).

Seyfarth, L. and Senker, J., "An NMR crystallographic approach for the determination of the hydrogen substructure of nitrogen bonded protons," *Phys Chem Chem Phys 11*(18):3522-3531, The Royal Society of Chemistry, England (Mar. 2009).

Smith, J.R., et al., "Analysis of Conformational Polymorphism in Pharmaceutical Solids Using Solid-State NMR and Electronic Structure Calculations," *J Phys Chem B 110*:7766-7776, American Chemical Society (2006).

Vogt, F.G., et al., "Solid-State NMR Analysis of Organic Cocrystals and Complexes," *Crystal Growth & Design 9*(2):921-937, American Chemical Society, United States (Feb. 2009).

Wi, S., et al., "Solid-State NMR and Quantum Chemical Investigations of $^{13}C^{\alpha}$ Shielding Tensor Magnitudes and Orientations in Peptides: Determining φ and ψ Torsion Angles," *J Am Chem Soc 127*:6451-6458, American Chemical Society (2005).

Wylie, B.J., et al., "Protein Structure Refinement Using $^{13}C^{\alpha}$ Chemical Shift Tensors," *J Am Chem Soc 131*:985-992, American Chemical Society, United States (Jan. 2009).

Zech, S.G., et al., "Protein Structure Determination by High-Resolution Solid-State NMR Spectroscopy: Application to Microcrystalline Ubiquitin," *J Am Chem Soc 127*:8618-8626, American Chemical Society, United States (2005).

\* cited by examiner

NMR CRYSTALLOGRAPHY METHODS FOR THREE-DIMENSIONAL STRUCTURE DETERMINATION

CROSS REFERENCE TO RELATED APPLICATIONS

This application claims the benefit of U.S. Prov. Appl. No. 61/389,158, filed Oct. 1, 2010, which is incorporated herein by reference in its entirety.

BACKGROUND OF THE INVENTION

1. Field of the Invention

The invention relates generally to methods for analyzing molecular structures. Among other things, the invention relates to new methods for determining the three-dimensional structure of a target compound using nuclear magnetic resonance (NMR) crystallography and new methods for screening test compounds having three-dimensional structures similar to that of a target compound.

2. Background Art

Acquiring the three-dimensional structure of pharmaceutical solids stands as one of the greatest obstacles to the rapid development of new and targeted drugs. Current methods are plagued by lengthy research timelines (often measured in months and years) and inherent experimental limitations. For instance, x-ray crystallography relies on the ability to grow consistent and sizable crystals of a compound, powder diffraction methods require a "best guess structural starting point," and computational methods are unreliable for all but the smallest, most rigid molecules.

Current NMR experiments allow access to virtually any feature of the nuclear Hamiltonian, i.e., dipole and quadrupolar coupling, chemical shift, etc. The nuclear Hamiltonian itself is so well characterized that ab initio quantum mechanical calculations are able to successfully compute NMR signals (such as chemical shielding and dipolar coupling) for a given molecular structure. Additionally, Solid-State NMR (SSNMR) has been shown to be a sensitive indicator of many structural features, including hydrogen bonding, stereochemistry, conformation, steric forces, and electrostatic interactions. Because of its sensitivity to structural features such as these, SSNMR has been employed during the last two decades to investigate a host of problems present in solids. This type of analysis became NMR crystallography when it was extended by three separate research groups in 2002 and 2003 to determine complete three-dimensional geometries (conformation) of molecular solids (the Griffin, Van Rossum, and Harper groups).

The first two research groups (Griffin and Van Rossum) studied similar molecules (peptide and protein, respectively) that had been isotopically labeled. See Rienstra, C. M. et al., PNAS 99:10260-10265 (2002) and Castellani, F. et al., Nature 420:98-102 (2002). They also used similar methods based on structural information gleaned from dipolar coupling. As with all SSNMR structural studies, they began by assigning the individual chemical shift values to corresponding nuclear sites in the molecule. Then, using dipolar coupling experiments at various mixing times (for both identical and dissimilar nuclear species), they were able to correlate both long range and short range atomic distances, and torsional angles. These introduced a series of inter-atomic constraints, which were used as a starting-place in the subsequent conformational search. Both research groups used a simulated annealing technique, a method that stochastically samples the space of allowed conformations. In this method, molecular potentials are configured to permit transitions among the multiple conformations consistent with the structural constraints. Griffin acknowledged that this method did not ensure that all regions of conformational space were sampled and thus employed a parallel technique to add additional rigor and certainty to his final result.

This second technique divided the search space into discrete nonoverlapping volumes and assigned each volume as allowed or disallowed, based on whether or not it contained viable structures. By eliminating structures that violated the NMR-imposed structural constraints, he found that there remained 56,975 allowed structures. Unlike Griffin, Van Rossum did not attempt to address the deficits of simulated annealing techniques (in particular, the lack of an exhaustive con formational search) and merely applied the method in order to find a solid-state magic angle spinning (MAS) NMR structure that satisfactorily described certain constraints he had uncovered.

Harper's method, published only months after Griffin and Van Rossum, was fundamentally different from the studies of those scientists. First, he used a small biomolecule (ambuic acid) at natural abundance, rather than using a large peptide that had been isotopically labeled to enhance the NMR signal. Like Griffin and Van Rossum, he began by assigning the $^{13}C$ shift values to the appropriate nuclear sites. After this, Harper's method diverges from the other studies. See Harper, J. K. et al., J. Org. Chem. 68:4609-4614 (2003). Both Griffin and Van Rossum had used dipolar coupling as the NMR values of interest, but Harper used NMR chemical shift principal values (CSPVs) as the experimental foundation for his work. He used Alderman's FIREMAT technique to acquire the CSPVs for each nuclear position, and compared these with a series of calculated conformers. See Alderman, D. W. et al., Mol. Phys. 95:1113-1126 (1998). Ambuic acid is a relatively small molecule with a six membered ring as the central feature and two short sidechains. He searched through conformational possibilities by examining different structural features independently and creating a set of possibilities that he thought were "reasonable" in some instances (i.e., intramolecular hydrogen bonding conformations) and exploring the conformations of other moieties in the structure by rotating around bonds in 30 degree increments. Harper also explored possible intermolecular hydrogen bonding schemes in ambuic acid by hypothesizing the existence of a dimeric structure and calculating the shifts for the dimeric compound. He admitted that this analysis scheme was not an exhaustive conformational search and further wrote that the inclusion of all combinations of conformational changes was "avoided due to the great increase in number of computations heeded."

After these NMR crystallography studies in 2002/2003, other research groups began to build upon these methods and to exploit structural features of molecules using SSNMR. The methods used by more recent NMR crystallography groups introduce subtle improvements to the methods proposed by those first three studies. However, all of these methods are tremendously expensive, not simply because of man-hours and experimental requirements, but most notably because of the overwhelming search of conformational space. The reason for this difficulty lies in the number of factors contributing to the NMR signal. Although single-crystal X-ray diffraction may enjoy a 1:1 correlation between real and reciprocal space, there is not an equivalent transformation from NMR that will yield a unique set of molecular coordinates. The researcher must therefore cull an enormous number of computationally generated polymorphs, compute theoretical NMR values for these, and contrast the theory with experimental NMR results. Obviously, the number of polymorphic possibilities increases exponentially with molecular size, ultimately prohibiting a complete conformational search. Although different methods have been attempted to reduce the total number of possible conformers, ultimately, NMR crystallographers must either submit to the systematic exhaustive search, limit themselves to the study of small or rigid molecules, or resign themselves to a high degree of inaccuracy in their results. Accordingly, current NMR crystallography techniques are iterative, costly, slow, and lacking in general application.

The pharmaceutical industry stands to benefit immensely should NMR crystallography become sufficiently accurate and robust so that it can be applied on a routine basis to characterize biologically relevant molecules. The impact on the pharmaceutical industry is further discussed below.

Distinct polymorphs of the same molecule may have significantly different solubility and thermodynamic stability. The thermodynamic properties of a given polymorph are extremely important to industrial manufacturing processes and storage. In one famous instance (the case of Abbott Laboratories' Norvir®), the manufactured formulation suddenly converted to a previously unobserved, more thermodynamically stable polymorph. The new polymorph was significantly less soluble (and less bioactive) than the previous form. This polymorphic "invasion" cost Abbott hundreds of millions of dollars trying to recover the first polymorph and an estimated $250 million in sales during the year the drug was withdrawn from the market. See Goho, A. "Tricky Business: The Crystal Form of a Drug can be the Secret to its Success" *Science News* 166:122-124 (2004).

Distinct polymorphs of the same molecule may have significantly different bioactivity. There are often distinct differences in bioactivity between two equivalently stable conformations. This means that the bioavailability and the overall biological activity of the drug in vivo may be different for two polymorphs of the same drug.

Thus, structural characterization is essential for pharmaceutical research and development. If molecular structures of investigational drugs could be consistently and accurately determined, it would significantly reduce the gap between the pace of discovery and development. Furthermore, it would also pave the way for greater throughput, and novel fields of research. Current methods create significant barriers of cost and time, discouraging all but the most promising of compounds from structural study. Removing this barrier will open up all biomolecules of interest to further study.

As mentioned above, burgeoning NMR crystallography methods are currently being used to determine molecular structure. Recent studies have shown NMR is capable of acquiring conformational features and even whole structures of samples that did not yield to analysis via other methods.

Effective drug research and design would benefit from a method that applies a combined SSNMR/computational approach in a swift and universally applicable manner. Thus, there is a need in the art for a fast, high-throughput method for determining the three-dimensional structure of a compound of interest. There is also a need, for example in rational drug design, for methods to quickly screen test compounds for those compounds that have a three-dimensional structure similar to that of a compound of interest.

BRIEF SUMMARY OF THE INVENTION

The present invention is a nuclear magnetic resonance (NMR) crystallography method. In it, data obtained from NMR experiments are used to determine the three-dimensional structure of a target compound and/or screen test compounds having a three-dimensional structure similar to that of a target compound.

One embodiment of the invention is directed to a method for determining the three-dimensional structure of a target compound by NMR crystallography, wherein the method comprises:

(a) identifying a set of reference compounds comprising similar substructures present in the target compound;

(b) obtaining NMR values for the target compound and both NMR values and atomic coordinates for equivalent atoms within the reference compounds;

(c) selecting a subset of reference compounds based upon the most suitable calculated relevant statistical match (rsm) for equivalent atoms in each reference compound identified in (a); and (d) obtaining and compiling the atomic coordinate data for equivalent atoms of reference compounds selected in (c) to generate a three-dimensional structure of the target compound.

In another embodiment, the equivalent atoms being compared between the reference compounds and the target compound are heavy atoms. In another embodiment, the reference compounds that are identified have identical substructures as those present in the target compound. In another embodiment, the rsm is the root mean square (rms) value for equivalent atoms in identified reference compounds. In yet another embodiment, the most suitable rsm is the lowest rms value calculated for equivalent atoms in each identified reference compound.

In one aspect of the invention, the identification of reference compounds is performed by a processor. In another aspect of the invention, the selection of reference compounds is performed by a processor. In one aspect of the invention, the NMR values of reference compounds are obtained by experimental measurement. In another aspect of the invention, the NMR values of reference compounds are obtained by calculation.

In another aspect of the invention, the NMR values and atomic coordinates for equivalent atoms within the reference compounds are obtained from a database. In a further aspect of the invention, the database is the Cambridge Structural Database.

In another embodiment, the invention requires the generation of substructures of the target compound before reference compounds are identified. In another embodiment, the invention requires a two-dimensional drawing of the target compound, NMR values of a preselected nuclear species contained within the target compound, and a database that comprises both NMR values of the same preselected nuclear species and atomic coordinate data for reference compounds to be obtained before generating substructures of the target compound. In another aspect of the invention, the database to be used is the Cambridge Structural Database.

In another embodiment, the invention is directed to a method for determining the three-dimensional structure of a target compound that further comprises displaying the generated three-dimensional structure of the target compound. In another aspect, the methods of the invention further comprise refining the generated three-dimensional structure. In another aspect, the methods of the invention further comprise determining one or more additional crystallographic features of the target compound, such as unit cell parameters, space group, and long range order.

In another embodiment, the invention is directed to a method of screening for test compounds having three-dimensional structures similar to that of a target compound, wherein the method comprises:

(a) providing two-dimensional drawings of the test compounds, NMR values of a preselected nuclear species contained within the test compounds, NMR values of the same preselected nuclear species for the target compound, and atomic coordinate data for the target compound;

(b) selecting a first atom of the target compound;

(c) generating a substructure of the target compound that includes all other atoms within the target compound that are separated by no more than 6 chemical bonds from the heavy atom;

(d) identifying a set of test compounds comprising substructures similar to the target compound substructure generated in (c);

(e) calculating rsm values for each of the test compounds identified in (d);

(f) selecting from the test compounds identified in (d), a subset of the test compound having the most suitable calculated rsm value;

(g) repeating (c)-(f) for each of the remaining atoms of the target compound;

(h) calculating global rsm values for each of the test compounds selected in (f); and (i) selecting from the test compounds identified in (f), the test compound having the lowest calculated global rms value. In one aspect of the invention, the identification of test compounds in (d) is performed by a processor. In another aspect of the invention, the selection of test compounds in (f) is performed by a processor. In yet another aspect of the invention, the selection of test compounds in (i) is performed by a processor. In one aspect of the invention, the NMR values of test compounds in (d) are obtained by experimental measurement. In another aspect of the invention, the NMR values of test compounds in (d) are obtained by calculation.

In another embodiment, the equivalent atoms being compared between the test compounds and the target compound are heavy atoms. In another embodiment, the rsm is the root mean square (rms) value for equivalent atoms in each identified test compound. In yet another embodiment, the most suitable rsm is the lowest rms value calculated for equivalent atoms in each identified test compound.

In one embodiment, the methods of the invention are automated. Another embodiment of the invention is directed to an apparatus configured to perform methods for determining the three-dimensional structure of a target compound or methods of screening for test compounds having three-dimensional structures similar to that of a target compound.

Another embodiment of the invention is directed to a reference compound identifier for use in methods for determining the three-dimensional structure of a target compound.

Another embodiment of the invention is directed to a test compound identifier for use in methods of screening for test compounds having three-dimensional structures similar to that of a target compound.

Another embodiment of the invention is directed to a server configured to obtain NMR values in methods for determining the three-dimensional structure of a target compound or methods of screening for test compounds having three-dimensional structures similar to that of a target compound.

BRIEF DESCRIPTION OF THE DRAWINGS/FIGURES

FIG. 1 depicts the structure and numbering of prednisolone tert-butylacetate (PTB).

Figure 2:
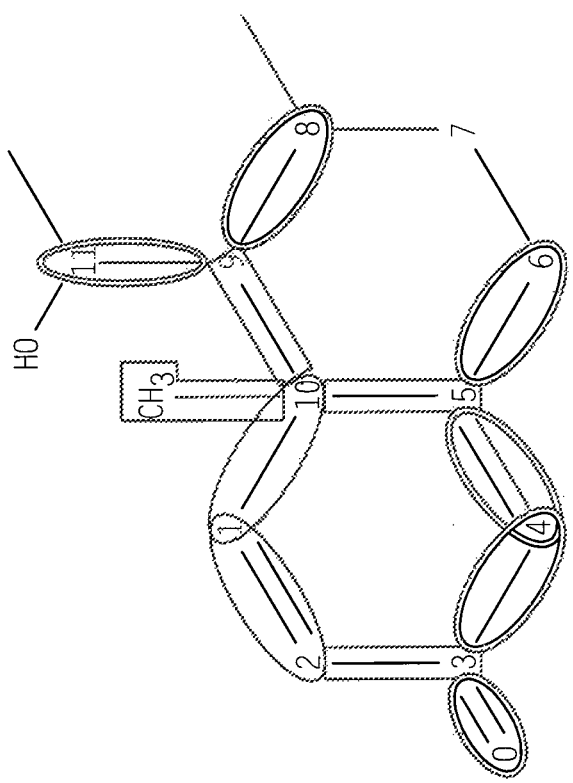
Figure 2:
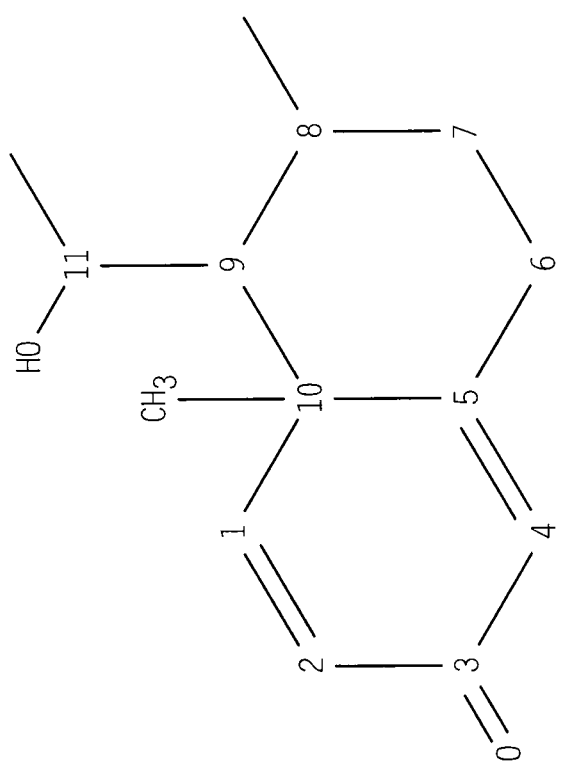

FIG. 2 depicts the C1 substructure used as the search parameter in the Cambridge Structural Database. Boxed and circled lines indicate structural features influencing the C1 position. Single-lined ovals=primary, boxed lines=secondary, double-lined ovals=tertiary. Also included are descriptor atoms in the substructure: C7 and the OH group at the C11 position.

Figure 3A:
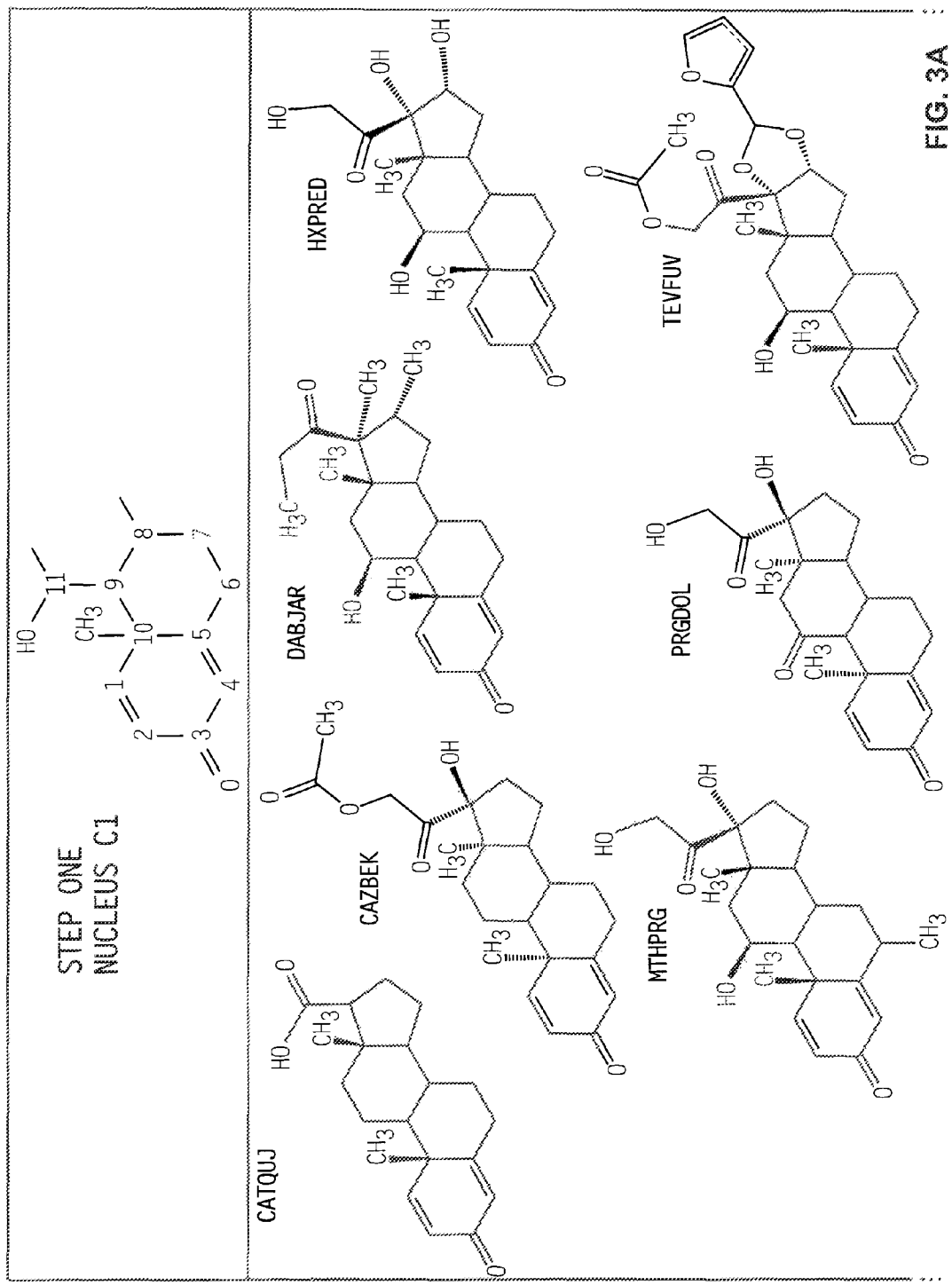
Figure 3B:
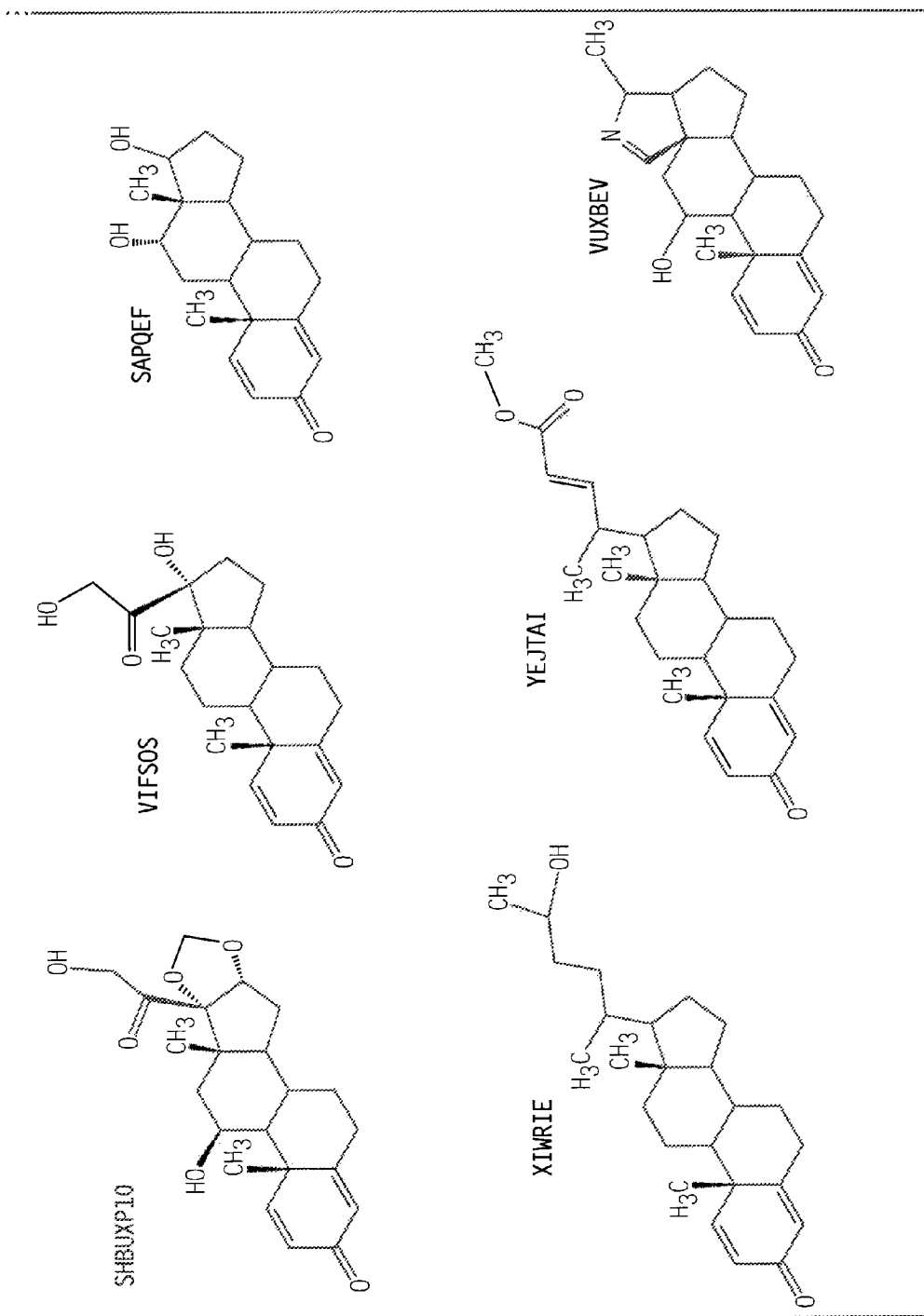

FIG. 3 displays a subset of the 24 reference compound structures selected from the Cambridge Structural Database (CSD) containing the C1 substructure for PTB. These 13 reference compound structures are identified by the names given in the CSD. The size and features of reference compounds significantly vary from one to another. The directional preference of the $CH_3$ group at the C10 position has been generalized (i.e. the stereo-up bond in CATQUJ versus the stereo-down bond in CAZBEK).

Figure 4:
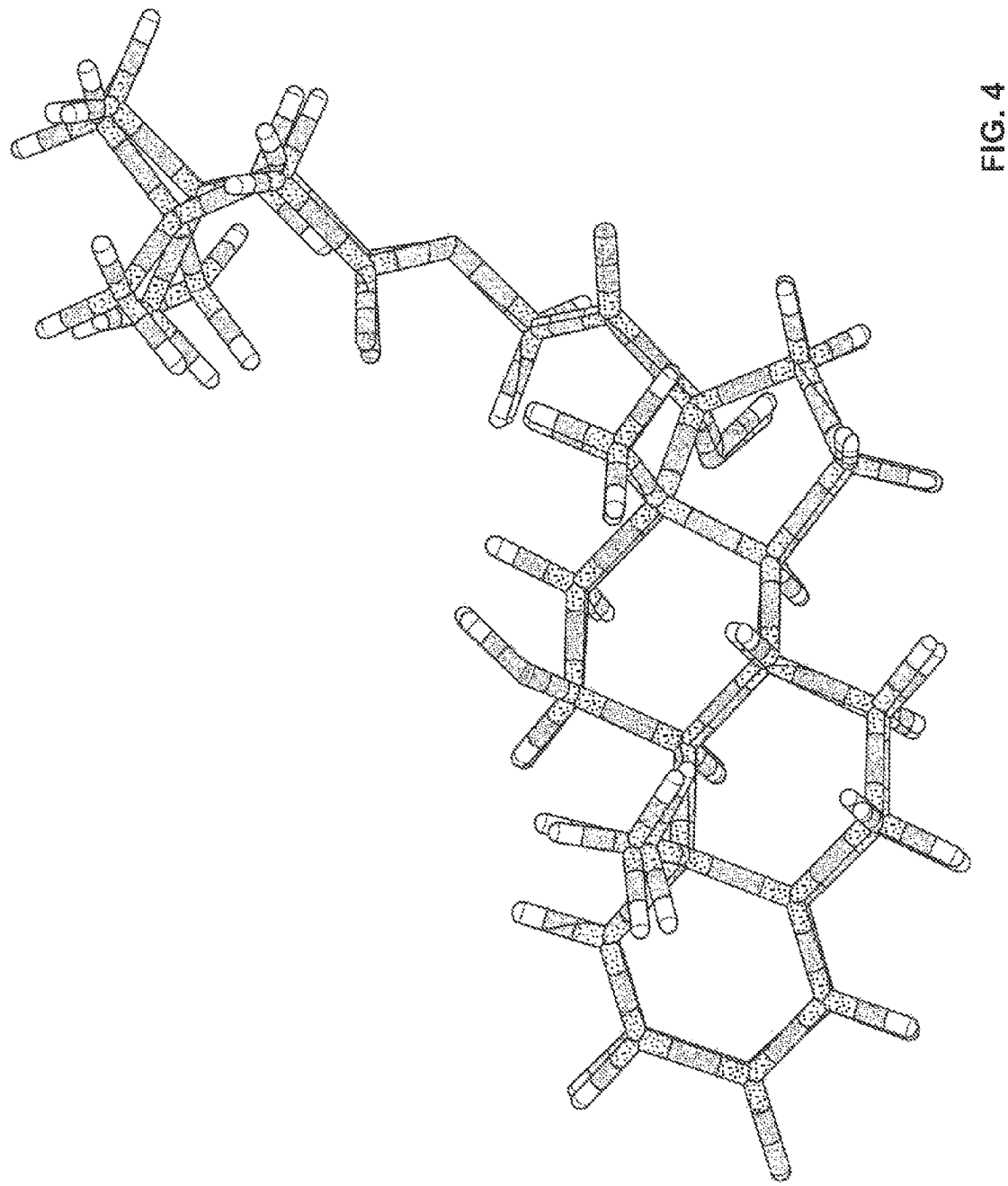

FIG. 4 is an overlay of the X-ray crystal structure and molecular coordinates for PTB obtained by this structural study following the claimed invention. Hydrogen atoms were added to X-ray coordinates. By following the methods of the invention, the generated three-dimensional structure of PTB deviates from the known crystal structure of PTB by a root mean square distance (rmsd) of 0.081.

DETAILED DESCRIPTION OF THE INVENTION

The present invention is directed to a technique that would enable the rapid mapping of conformational space of any structure and allow the three-dimensional structure of that solid to be determined. The present invention requires that the researcher possess only two pieces of data in order to determine conformation: the two-dimensional chemical diagram of the molecule and its solid state NMR values. These NMR values may be experimentally measured or calculated and may be represented by chemical shift principal values (CSPVs) or chemical shift tensors (CSTs).

DEFINITIONS

Non-limiting examples of "target compounds" for use in the claimed methods are discussed in later sections of this specification. The target compound may be a molecule for which a three-dimensional structure is sought or a molecule that provides a template for screening test compounds with similar three-dimensional structures.

As used herein, "substructure" is defined as a portion of a molecule comprised of two or more atoms.

As used herein, "similar substructures" are defined as substructures of reference or test compounds that share at least 50% identity with a given substructure of a target compound in terms of molecular composition, bond connectivity, and bond type. In one aspect of the invention, similar substructures of reference or test compounds share from about 50% to about 100% identity with a corresponding substructure of a target compound. In another aspect of the invention, similar substructures of reference or test compounds share from about 75% to about 95% with a corresponding substructure of a target compound. In another aspect of the invention, similar substructures of reference or test compounds share from about 80% to about 90% with a corresponding substructure of a target compound. In another aspect of the invention, similar substructures of reference or test compounds share about 50%, 55%, 60%, 65%, 70%, 75%, 80%, 85%, 90%, 95%, or 100% with a corresponding substructure of a target compound.

As used herein, "similar three-dimensional structures" are defined as three-dimensional structures of test compounds that share at least 50% identity with the three-dimensional structure of a target compound in terms of molecular composition, bond connectivity, bond type, and spatial arrangement. In one aspect of the invention, similar substructures of test compounds share from about 50% to about 99% identity with the three-dimensional structure of a target compound. In one aspect of the invention, similar substructures of test compounds share from about 75% to about 95% identity with the three-dimensional structure of a target compound. In one aspect of the invention, similar substructures of test compounds share from about 80% to about 90% identity with the three-dimensional structure of a target compound. In another aspect of the invention, similar substructures of test compounds share about 50%, 55%, 60%, 65%, 70%, 75%, 80%, 85%, 90%, 95%, or 99% identity with the three-dimensional structure of a target compound As used herein, the "three-dimensional structure" of a target compound is defined as the unique spatial arrangement of atoms within a target compound. The three-dimensional structure of a target compound does not require the spatial information for all atoms of the target compound to be known or displayed. For instance, a three-dimensional structure of a target compound can include the portion of the target compound that binds to a biological macromolecule of interest or can exclude atoms that are related by symmetry, e.g., equivalent terminal methyl groups of PTB.

As used herein, "relevant statistical match" is defined as the difference between the NMR values of an atom of the target compound and the corresponding NMR values of an equivalent atom in each one of the reference or test compounds. Relevant statistical match is abbreviated as "rsm" throughout the specification.

The rsm may be obtained by any one of the following: (i) measuring the goodness of fit between the NMR values of an atom of the target compound and the corresponding NMR values of an equivalent atom in each one of the reference or test compounds, (ii) using a statistical method to sort between the goodness of fit between NMR values of an atom of the target compound and the corresponding NMR values of an equivalent atom in a set of reference or test compounds, (iii) using a statistical method to select a reference or test compound with NMR values that most closely adhere to the NMR values of analogous atoms in the target compound; or (iv) using a statistical method to eliminate reference or test compounds that are poor statistical matches to the NMR values of the target compound. In one embodiment, the rsm is obtained by using an F-test.

The rsm includes, but is not limited to, the root mean square (rms) of the difference between the NMR values of an atom of the target compound and the corresponding NMR values of an equivalent atom in each one of the reference compounds. Root mean square is abbreviated as "rms" throughout the specification. Rms values can be calculated based on the distances between NMR chemical shift principal values according to Alderman, D. W. et al., *J. Magn. Reson. Ser. A.* 101:188-197 (1993), which is herein incorporated by reference in its entirety.

The "most suitable" calculated rsm can be, but is not limited to, any one of the following: the lowest calculated rsm among the reference compounds, a calculated rsm value that cannot be eliminated with more than 75% probability from the set of rsm values in the reference compounds by a statistical test, a calculated rsm value that is no more than $2\sigma$ different than the lowest calculated rsm among the reference compounds, a calculated rsm value that is among the lowest calculated rsm among the reference compounds, and a calculated rsm value that differs by no more than 85% from the lowest calculated rsm from among the reference compounds.

"Global rms value" is defined as the sum of the differences between the NMR values of each of the atoms of the target compound and the corresponding NMR values of each of the equivalent atoms of a test compound.

As used herein, "nuclear magnetic resonance" is defined as a non-destructive spectroscopic method whereby the magnetic properties of the nuclei within a sample are probed through the application of an external magnetic field and radiofrequency pulses. The energy levels of the nuclei correspond to the orientations of their magnetic moment within the external field. Nuclear magnetic resonance is abbreviated as "NMR" throughout the specification.

As used herein, "solid-state nuclear magnetic resonance" is defined as a kind of NMR spectroscopic method characterized by the presence of anisotropic interactions. Solid-state nuclear magnetic resonance is abbreviated as "SSNMR" throughout the specification.

Where a substructure of a target compound is generated with respect to a specific atom of interest within the target compound and similar substructures are identified among reference or test compounds, the atoms of identified reference or test compound substructures that share the same relative two-dimensional position, i.e., the reference or test compound atoms share the same local environment as the specific target compound atom of interest (e.g., the atoms share the same bonds and are neighbors to the same types of atoms), are defined as "equivalent" atoms.

Chemical shift tensor is abbreviated as "CST" throughout the specification. The CST of a given nuclear spin is a second rank tensor that gives the coupling of that spin to the local induced magnetic environment. The CST may be written as a 3×3 matrix in the reference frame of the nuclei in question. The CST depends upon the orientation of the sample's atomic framework within the static magnetic field. It is possible to rotate the CST into its principal axis system (PAS) in which the off-diagonal terms are zero. In the PAS, the tensor may be described by its diagonal elements and the three Euler angles, specifying the PAS orientation with respect to the molecular coordinate system. The terms along the diagonal are called the chemical shift principal values. Chemical shift principal value is abbreviated as "CSPV" throughout the specification. The CSPVs are observed in solid-state NMR when the sample consists of a microcrystalline powder. In this instance, the unit cell remains intact but the crystallites assume all possible orientations and the off-diagonal tensor values are, therefore, lost.

As used herein, "CSD" denotes the Cambridge Structural Database.

As used herein, "CCDC" denotes the Cambridge Crystallographic Data Center.

Underlying Concepts

The functioning of the present invention rests on four independent concepts that when combined become a powerful tool to wide scale implementation of NMR crystallography.

The first and second concepts underlying the present invention are well-established features of NMR. The first concept underlying the present invention constitutes the main premise of current NMR crystallography—that the NMR chemical shift tensor (CST) is sensitive to structure. This principle has been well established by many sources. The CST captures the electronic influences of an atom's neighbors through infinitesimal alterations to its spin. CSTs therefore manifest hydrogen bonding, stereochemistry, conformation, steric constraints, electrostatic interactions and lattice (CSTs encode lattice effects either through direct electromagnetic influence or indirectly, via molecular conformation). Extracting structural information from the CST is the aim of NMR crystallography. It is also an aim of the present invention.

The second concept underlying the present invention is the sensitivity of the CST to nearby atomic arrangements. In fact, the sensitivity is primarily a local phenomenon, i.e., atoms more than three bonds distant or a few Å from a given position have little influence on the CST. See Pretsch, E. et al., *Tables of Spectral Data for Structural Determination of Organic Compounds*, Springer-Verlag pp. c10-c265 (1989) and Grant, D. M., *Encyclopedia of Magnetic Resonance*, Wiley 2:1298 (1996). The researcher may therefore exclude distant structural features from consideration when using the CST to study molecular shape.

Consider the case of two molecules that share a common set of features such as an identical arrangement of certain functional groups. Now, consider a nuclear position located within the identical portions, sufficiently distant from any stereochemical features that differ between the molecules. One may then say that this nuclear position is analogous between the two molecules. Accordingly, it becomes possible to compare the CSTs between these nuclei. Because they share local stereochemistry, variations between the CSTs at the target nuclei location will primarily reflect local conformational differences between the two molecules.

The first two concepts underlying the present invention lead one to understand that the CST can reveal structural differences between two molecules. The presumption is that there are two molecules with features that one wishes to judge between. In order to find these molecules for comparison, the third and fourth concepts underlying the present invention are discussed.

Margaret Etter's work forms the basis for the third concept underlying the present invention, i.e., there exist intramolecular and intermolecular conformational preferences in crystal structures. Etter exposed this concept in 1990 while developing a rationale for hydrogen bonding in organic solids. In the decades prior to her research, crystallographers considered polymorphism and crystal packing too complex to understand. Etter revealed, however, that patterns in hydrogen bonds emerge from this apparent randomness. In her seminal paper, "Encoding and Decoding Hydrogen-Bond Patterns of Organic Compounds," she formulated a method (graph set) to meticulously categorize and describe the patterns formed by hydrogen bonds in crystal structures. See Etter, M. C. *Acc. Chem. Res.* 23:120-126 (1990). In doing so, she uncovered "laws" governing crystallization and polymorphism, and demonstrated that nature has predilections in the way molecules assemble to form a lattice. In particular, she noticed that the patterns formed by hydrogen bonds gave an excellent description of the orientations of functional groups with one another. Etter wrote about this discovery in the following way: "different functional group classes show clear preferences for specific hydrogen-bond patterns in their crystal structures, despite the presence of other unpredictable and nonspecific lattice forces."

Furthermore, Etter found that both local conformation and lattice arrangement tended towards geometries that favored sequences of hydrogen bonding. After painstaking cataloguing of hydrogen bond patterns in crystal structures, researchers explained this preferred lattice assembly in terms of cooperativity or non-additivity. This phenomenon occurs when the hydrogen-bond energy of a network or motif is greater than the sum of the energy of the individual hydrogen bonds. See Jeffrey, G. A., *Crystall. Rev.* 9:135-176 (2003).

Understanding that a correlation exists between lattice energy, local conformation, and hydrogen bonding is useful for crystallographers. The motifs created by hydrogen bonds sort, describe, and explain crystallization and polymorphism, allowing the researcher to deconstruct the "reasons" behind a particular lattice assembly. But Etter's graph set theory of hydrogen bonding is used to explain structure, not predict it. Researchers may categorize known crystal structures according to their hydrogen bonds, but this does very little for predicting other lattice structures. Researchers cannot posit new crystals based solely on the notion that hydrogen bonding tends to occur between moieties, functional groups, or molecules. Furthermore, even if such an application were included as part of computational lattice energy minimization, there is no guarantee that the method would chance upon a crystal structure (however thermodynamically favorable) that actually existed in nature.

The present invention uses the implications of Etter's method as a predictive tool by recognizing that one need not analyze each possible conformational preference in terms of its hydrogen bonding rationale. In fact, one does not need to consider hydrogen bonding at all. Rather, one must simply acknowledge that nature has sorted crystals into hydrogen bonding preferences.

The fourth concept underlying the present invention recognizes the wealth of structural information available in structural databases which represents many (and in many cases, all) probable assemblies of functional groups with one another. Consider that, as observed by Etter and others, the geometries of functional groups are limited to a set of probable conformations. The researcher may then find geometrical trends in particular sets of moieties by examining representative samples available in a large crystallography database. A randomly selected set of molecules sharing the same relative collection of functional groups will provide the range of likely relative conformations of these functional groups. In other words, available crystal structures provide precedents for likely conformations.

This realization represents a significant boon to conformational searches. Current methods that exploit the influence of conformational variation on tensor values must search an infinite variety of possible geometries. The four concepts underlying the present invention allow one to recognize that one need only examine the most probable conformations. In other words, one need only examine those conformations that actually exist in nature—and those that exist in nature are represented in a comprehensive structural database. NMR may be used to compare and sort these values.

Method for Determining Three-Dimensional Molecular Structure

The four concepts underlying the present invention, when used in concert, become a radically effective structure prediction tool. Consider the application of the present invention to determine the three-dimensional conformation of an unknown organic microcrystalline solid, molecule X. Assume that the two-dimensional chemical diagram for molecule X is known and that the experimental CSPVs of the $^{13}$C nuclei in the sample have been acquired (other nuclei may also be used).

One begins by examining the two-dimensional chemical diagram of molecule X one atomic nucleus at a time. At each heavy atom position, a substructure is created comprised of those features that will likely influence its chemical shift. The substructure primarily excludes structural features beyond three bond lengths. One then uses these substructures as search parameters in a crystallographic structure database query. The present invention can make use of a Cambridge Crystallographic Data Centre (CCDC) PROquest query. Such search identifies molecules that share the stereochemistry of the substructure, but whose conformations differ from one another. These "identified reference compounds" represent likely conformations of the substructure. Differences between the CSPVs of identified reference compounds' heavy atoms reflect conformational differences between the identified reference compounds.

The CSPVs of these selected reference compounds are evaluated against experimentally measured or calculated CSPVs of the target compound. Identified reference compounds with poor CSPV matches at the equivalent heavy atom positions can be eliminated and the remaining identified reference compounds can be selected as probable conformers for each substructure.

The geometries of the substructures can be confirmed by combining the structural information gleaned from all equivalent heavy atoms.

A compilation of all selected substructure geometries yields the complete conformation of the target compound.

The process described above can be automated. The series of "if, then" steps can be easily used in routine computational execution. Automation significantly cuts down on the time needed to determine the probable conformation of a particular molecule.

Accordingly, one embodiment of the invention is directed to a method for determining the three-dimensional structure of a target compound by NMR crystallography, wherein the method comprises:

(a) identifying a set of reference compounds comprising similar substructures present in the target compound;

(b) obtaining NMR values for the target compound and both NMR values and atomic coordinates for equivalent atoms within the reference compounds;

(c) selecting a subset of reference compounds based upon the most suitable calculated relevant statistical match (rsm) for equivalent atoms in each reference compound identified in (a); and (d) obtaining and compiling the atomic coordinate data for equivalent atoms of reference compounds selected in (c) to generate a three-dimensional structure of the target compound.

In another embodiment, the invention is directed to a method for determining the three-dimensional structure of a target compound by NMR crystallography, wherein the method comprises:

(a) identifying a set of reference compounds comprising similar substructures present in the target compound;

(b) obtaining NMR values for the target compound and both NMR values and atomic coordinates for equivalent heavy atoms within the reference compounds;

(c) selecting a subset of reference compounds based upon the most suitable calculated rsm for equivalent heavy atoms in each reference compound identified in (a); and (d) obtaining and compiling the atomic coordinate data for equivalent heavy atoms of reference compounds selected in (c) to generate a three-dimensional structure of the target compound.

In yet another embodiment, the invention is directed to a method for determining the three-dimensional structure of a target compound by NMR crystallography, wherein the method comprises:

(a) identifying a set of reference compounds comprising identical substructures present in the target compound;

(b) obtaining NMR values for the target compound and both NMR values and atomic coordinates for equivalent heavy atoms within the reference compounds;

(c) selecting a subset of reference compounds based upon the lowest calculated root mean square (rms) value for equivalent heavy atoms in each reference compound identified in (a); and (d) obtaining and compiling the atomic coordinate data for equivalent heavy atoms of reference compounds selected in (c) to generate a three-dimensional structure of the target compound. In one aspect of the invention, the identification of reference compounds in (a) is performed by a processor. In another aspect of the invention, the selection of reference compounds in (c) is performed by a processor. In one aspect of the invention, the NMR values of reference compounds in (a) are obtained by experimental measurement. In another aspect of the invention, the NMR values of reference compounds in (a) are obtained by calculation.

In yet another embodiment, the relevant statistical match is the root mean square (rms) value. In one embodiment, the rms value can be calculated as the difference between the CSPV of an atom of the target compound and the corresponding CSPV of an equivalent atom in each one of the reference compounds. In another embodiment, the rms value can be calculated as the difference in the dipolar coupling value of an atom of the target compound and the corresponding dipolar coupling value of an atom of each one of the identified reference compounds.

In a specific embodiment, the invention is directed to a method for determining the three-dimensional structure of a target compound by NMR crystallography, wherein the method comprises:

(a) generating substructures of the target compound;

(b) identifying a set of reference compounds comprising the identical substructures generated in (a);

(c) obtaining NMR values for the target compound and both NMR values and atomic coordinates for reference compounds;

(d) calculating rms values for equivalent heavy atoms in each reference compound identified in (b);

(e) selecting from the reference compounds identified in (b), a subset of reference compounds having the lowest calculated rms values; and (f) obtaining and compiling the atomic coordinate data for the equivalent heavy atoms of the reference compounds selected in (e) to generate a three-dimensional structure of the target compound. In one aspect of the invention, the identification of reference compounds in (b) is performed by a processor. In another aspect of the invention, the selection of reference compounds in (e) is performed by a processor. In one aspect of the invention, the NMR values of reference compounds in (b) are obtained by experimental measurement. In another aspect of the invention, the NMR values of reference compounds in (b) are obtained by calculation. In another aspect of the invention, the NMR values and atomic coordinates for equivalent atoms within the reference compounds are obtained from a database.

Another embodiment of the invention is directed to a method for determining the three-dimensional structure of a target compound, wherein the method comprises:

(a) obtaining a two-dimensional drawing of the target compound, NMR values of a preselected nuclear species contained within the target compound, and a database that comprises both NMR values of the same preselected nuclear species and atomic coordinate data for reference compounds;

(b) selecting a first heavy atom of the target compound;

(c) generating a substructure of the target compound that includes all other heavy atoms within the target compound that are separated by no more than 3 chemical bonds from the heavy atom;

(d) identifying a set of reference compounds comprising the identical substructure generated in (c) in the database;

(e) calculating rms values for each of the reference compounds identified in (d);

(f) selecting from the reference compounds identified in (d), the reference compound having the lowest calculated rms value;

(g) obtaining the atomic coordinate data for the equivalent heavy atom of the selected reference compound of (f);

(h) repeating (c)-(g) for each of the remaining heavy atoms of the target compound; and (i) compiling all of the atomic coordinate data obtained in (g) to generate a three-dimensional structure of the target compound. In one aspect of the invention, the identification of reference compounds in (d) is performed by a processor. In another aspect of the invention, the selection of reference compounds in (f) is performed by a processor. In one aspect of the invention, the NMR values of reference compounds in (d) are obtained by experimental measurement. In another aspect of the invention, the NMR values of reference compounds in (d) are obtained by calculation. In yet a further aspect, the database is the Cambridge Structural Database.

One aspect of the invention includes calculating chemical shifts and chemical shielding for the generated three-dimensional structure and comparing the calculated chemical shifts and calculated chemical shielding to the chemical shifts and chemical shielding obtained by experimental measurement for the target compound.

In one aspect of the invention, NMR values can be calculated or measured, or both calculated and measured, from one or more of the following types of interactions: Zeeman interactions, quadrupolar interactions, dipolar couplings, paramagnetic interactions, chemical shift, chemical shielding, and J-couplings. In a specific embodiment, the NMR values are calculated or measured from chemical shift and chemical shielding.

In another aspect of the invention, the NMR values can be obtained from a nuclear species such as, but not limited to, $^1$H, $^{13}$C, $^{15}$N, $^{17}$O, and $^{31}$P. In a further aspect, the NMR values are obtained from a nuclear species in said target compound that is selected from the group consisting of: $^{13}$C, $^{15}$N, $^{17}$O, and $^{31}$P. In yet a further aspect, the nuclear species in the target compound is $^{13}$C. Heavy atoms are defined as those atoms other than $^1$H.

In one aspect of the invention, the nuclear species is at natural abundance. In another aspect of the invention, the nuclear species is isotopically labeled. Non-limiting exampled of isotopes suitable for use in the present invention, include $^1$H, $^{13}$C, $^2$H, $^{10}$B, $^{11}$B, $^{14}$N, $^{15}$N, $^{17}$O, $^{19}$F, $^{23}$Na, $^{29}$Si, $^{31}$P, $^{35}$Cl, $^{113}$Cd, $^{129}$Xe, and $^{195}$Pt.

In one aspect of the invention, the target compound for three-dimensional structure determination has a molecular weight from about 100 to about 200,000 Daltons. In one aspect of the invention, the target compound has a molecular weight of about 100, 200, 500, 1000, 2000, 5000, 10,000, 20,000, 50,000, 100,000, 150,000, or 200,000 Daltons. In another aspect of the invention, the target compound has a weight from about 100 to about 1000 Daltons. In another aspect of the invention, the target compound has a molecular weight from about 100 to about 500 Daltons. In another aspect of the invention, the target compound has a weight from about 500 to about 1000 Daltons. In another aspect of the invention, the target compound has a weight from about 1000 to about 2000 Daltons. In another aspect of the invention, the target compound has a weight from about 2000 Daltons to about 5000 Daltons. In another aspect of the invention, the target compound has a weight from about 5000 Daltons to about 10,000 Daltons. In another aspect of the invention, the target compound has a molecular weight from about 100 to about 10,000 Daltons. In another aspect of the invention, the target compound has a weight from about 10,000 to about 20,000 Daltons. In another aspect of the invention, the target compound has a weight from about 20,000 to about 50,000 Daltons. In another aspect of the invention, the target compound has a weight from about 50,000 to about 100,000 Daltons. In another aspect of the invention, the target compound has a weight from about 100,000 to about 150,000 Daltons. In another aspect of the invention, the target compound has a weight from about 150,000 to about 200,000 Daltons. In another aspect of the invention, the target compound has a molecular weight from about 10,000 to about 200,000 Daltons.

In another aspect, the methods of the invention further comprise refining the generated three-dimensional structure based on measurements obtained for the target compound by one or more of the following techniques: x-ray diffraction, neutron diffraction, and electron diffraction. In a further aspect, the methods further comprise refining the generated three-dimensional structure based on powder x-ray diffraction, powder neutron diffraction, powder electron diffraction measurements, or combinations thereof, obtained for the target compound. In another aspect, the methods of the invention farther comprise refining the generated three-dimensional structure based on NMR measurements obtained for a second nuclear species in the target compound. Such second nuclear species can be, but is not limited to, $^1$H, $^{13}$C, $^{15}$N, $^{17}$O, and $^{31}$P. In another aspect, the methods further comprise refining the generated three-dimensional structure based on NMR values calculated or measured, or both calculated and measured, from one or more of the following types of interactions: Zeeman interactions, quadrupolar interactions, dipolar couplings, paramagnetic interactions, chemical shift, chemical shielding, and J-couplings.

In another aspect, the methods of the invention further comprise determining one or more additional crystallographic features of the target compound based on x-ray diffraction, neutron diffraction, or electron diffraction measurements obtained for the target compound, wherein the one or more additional crystallographic features is selected from the group consisting of: unit cell parameters, space group, and long range order. In another aspect, the methods of the invention further comprise determining one or more additional crystallographic features of the target compound based on NMR values obtained for a second nuclear species in the target compound, wherein the one or more additional crystallographic features is selected from the group consisting of: unit cell parameters, space group, and long range order. In yet another aspect, the methods of the invention further comprise determining one or more additional crystallographic features of the target compound based on NMR values calculated or measured, or both calculated and measured, from one or more of the following types of interactions: Zeeman interactions, quadrupolar interactions, dipolar couplings, paramagnetic interactions, chemical shift, chemical shielding, and J-couplings, wherein the one or more additional crystallographic features is selected from the group consisting of: unit cell parameters, space group, and long range order. For instance, the methods of the invention can determine the number of target compounds in the unit cell and their orientation with respect to one another.

In one aspect of the invention, the three-dimensional structure of the target compound is determined in 1, 2, 3, 4, 5, 6, 7, 8, 9, 10, 15, 20, 25, 30, 35, 40, 45, 50, or 55 minutes. In another aspect, the three-dimensional structure of the target compound is determined in 1, 2, 3, 4, or 5 hours. In another aspect of the invention, the three-dimensional structure of the target compound is generated in from about 1 minute to about 5 minutes. In another aspect of the invention, the three-dimensional structure of the target compound is generated in from about 5 minutes to about 10 minutes. In another aspect of the invention, the three-dimensional structure of the target compound is generated in from about 10 minutes to about 30 minutes. In another aspect of the invention, the three-dimensional structure of the target compound is generated in from about 30 minutes to about 1 hour. In another aspect of the invention, the three-dimensional structure of the target compound is generated in from about 1 hour to about 2 hours. In yet another aspect of the invention, the three-dimensional structure of the target compound is determined in from about 1 minute to about 2 hours. In yet another aspect of the invention, the three-dimensional structure of said target compound is determined in about 5 minutes. In yet another aspect of the invention, the three-dimensional structure of said target compound is determined from about 1 hour to about 1 month. In yet another aspect of the invention, the three-dimensional structure of said target compound is determined from about 1 month to about 3 years.

Target, Reference, and Test Compounds

Target, reference, and test compounds that can be used in the methods of the invention include for example, without limitation, synthetic organic compounds, chemical compounds, naturally occurring products, polypeptides and peptides, nucleic acids, etc. Essentially any chemical compound can be used in the methods of the invention.

In one embodiment, target compounds for use in the present invention can be charged or have a neutral charge. Target compounds can be organic small molecules, organic macromolecules, organometallic compounds, or salts.

In one embodiment, reference compounds for use in the present invention can be charged or have a neutral charge. Reference compounds can be organic small molecules, organic macromolecules, organometallic compounds, or salts.

In one embodiment, test compounds for use in the present invention can be charged or have a neutral charge. Test compounds can be organic small molecules, organic macromolecules, organometallic compounds, or salts.

In one embodiment, the methods of the invention require obtaining the NMR values and two-dimensional structures from a small organic molecule or peptide library.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation of combinatorial chemical libraries is well known to those of skill in the art. Such combinatorial chemical libraries include, but are not limited to, peptide libraries (see, e.g., U.S. Pat. No. 5,010,175; Furka *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries, peptide nucleic acid libraries (see, e.g., U.S. Pat. No. 5,539,083), carbohydrate libraries (see, e.g., Liang et al., *Science* 274:1520-1522 (1996) and U.S. Pat. No. 5,593,853), small organic molecule libraries (see, e.g., isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Asinex, Moscow, Russia; Tripos, Inc., St. Louis, Mo.; ChemStar, Ltd, Moscow, Russia; 3D Pharmaceuticals, Exton, Pa.; Martek Biosciences, Columbia, Md.; etc.).

Target, reference, and test compounds may comprise functional groups necessary for structural interaction with proteins, particularly hydrogen bonding, and can typically include at least an amine, carbonyl, hydroxyl or carboxyl group. The target, reference, and test compounds may comprise cyclical carbon or heterocyclic structures, and/or aromatic or polyaromatic structures substituted with one or more of the above functional groups. Target, reference, and test compounds are also found among biomolecules including peptides, saccharides, fatty acids, steroids, purines, pyrimidines, derivatives, structural analogs or combinations thereof.

Target Compound Compositions

Target compounds for three-dimensional structure determination can be found in a number of compositions. For example, the target compound can be found in a racemic composition. While the target compound can be found in a microcrystalline composition, it may also be found in an amorphous composition.

Non-limiting examples of where target compounds for three-dimensional structure determination can also be found include, but are not limited to, pharmaceutical, nutriceutical, or industrial compositions, organic complexes, zeolites, microporous solids, minerals, glasses, food products, ceramics, semiconductor materials, archaeological specimens, resins, inorganic complexes, mesophorous solids, aluminosilicates/phosphates, cements, wood, bones, metals and alloys, and polymers.

Three-dimensional structure determination may be used to determine the structure of a polymorph of a target compound. Three-dimensional structure determination may also be used for quality-control purposes, i.e., to ensure that all target compounds for use in a therapeutic or industrial process have the same three-dimensional structure (and therefore, will have the same stability and dissolving properties). Three-dimensional structure determination of a target compound can also be used as a starting point for rational drug design.

For example, the three-dimensional structure of a target compound can be solved after it has been conformationally constrained in the active site of a protein. One method by which the target compound can be conformationally constrained is by isotopically labeling it. Once the three-dimensional structure of this conformationally constrained target compound has been solved, test compounds with similar three-dimensional structures may be searched and screened. The benefits of determining the three-dimensional structure of a conformationally constrained target compound are many-fold: (i) a correlation can be made between the three-dimensional structure of the target compound and the toxicity and/or efficacy of the target compound; (ii) the three-dimensional shape or space of the protein active site can be mapped such that further suitable test compounds may be identified for therapeutic use; (iii) full or partial binding sites may be identified in the target compound such that further suitable test compounds may be identified for future use; and (iv) full or partial geometries of the bound target compound may be used to identify analogous small molecules with related bioactivities.

Methods for Screening Test Compounds

Accordingly, in another embodiment, the invention is directed to a method of screening for test compounds having three-dimensional structures similar to that of a target compound, wherein the method comprises:

(a) providing two-dimensional, drawings of the test compounds, NMR values of a preselected nuclear species contained within the test compounds, NMR values of the same preselected nuclear species for the target compound, and atomic coordinate data for the target compound;

(b) selecting a first atom of the target compound;

(c) generating a substructure of the target compound that includes all other atoms within the target compound that are separated by no more than 3 chemical bonds from the heavy atom;

(d) identifying a set of test compounds comprising substructures similar to the target compound substructure generated in (c);

(e) calculating rsm values for each of the test compounds identified in (d);

(f) selecting from the test compounds identified in (d), a subset of the test compound having the most suitable calculated rsm value;

(g) repeating (c)-(f) for each of the remaining atoms of the target compound;

(h) calculating global rsm values for each of the test compounds selected in (f); and (i) selecting from the test compounds identified in (f), the test compound having the lowest calculated global rms value.

In another embodiment, the invention is directed to a method of screening for test compounds having three-dimensional structures similar to that of a target compound, wherein the method comprises:

(a) providing two-dimensional drawings of the test compounds, NMR values of a preselected nuclear species contained within the test compounds, NMR values of the same preselected nuclear species for the target compound, and atomic coordinate data for the target compound;

(b) selecting a first heavy atom of the target compound;

(c) generating a substructure of the target compound that includes all other heavy atoms within the target compound that are separated by no more than 3 chemical bonds from the heavy atom;

(d) identifying a set of test compounds comprising substructures similar to the target compound substructure generated in (c);

(e) calculating rms values for each of the test compounds identified in (d);

(f) selecting from the test compounds identified in (d), the test compound having the lowest calculated rms value;

(g) repeating (c)-(f) for each of the remaining heavy atoms of the target compound;

(h) calculating global ins values for each of the test compounds selected in (1); and (i) selecting from the test compounds identified in (f), the test compound having the lowest calculated global rms value.

In one aspect of the invention, the NMR values of test compounds identified in (d) are obtained by experimental measurement. In another aspect of the invention, the NMR values of test compounds identified in (d) are obtained by calculation. In another aspect of the invention, identification of test compounds in (d) is performed by a processor. In another aspect of the invention, the selection of test compounds in (f) is performed by a processor. In another aspect of the invention, the selection of test compounds in (i) is performed by a processor.

NMR values can be calculated or measured, or both calculated and measured, from one or more of the following types of interactions: Zeeman interactions, quadrupolar interactions, dipolar couplings, paramagnetic interactions, chemical shift, chemical shielding, and J-couplings. In a specific embodiment, the NMR values are calculated or measured from chemical shift and chemical shielding.

In another aspect of the invention, the NMR values are obtained from a nuclear species in the target compound, such as, but not limited to, $^{1}H$, $^{13}C$, $^{15}N$, $^{17}O$, and $^{31}P$. In a further aspect, the NMR values are obtained from a nuclear species in the target compound that is selected from the group consisting of: $^{13}C$, $^{15}N$, $^{17}O$, and $^{31}P$. In yet a further aspect, the nuclear species in the target compound is $^{13}C$.

In one aspect of the invention, the nuclear species is at natural abundance. In another aspect of the invention, the nuclear species is isotopically labeled.

In one aspect of the invention, the target compound for use in methods of screening test compounds having similar three-dimensional structures as a target compound has a molecular weight from about 100 to about 200,000 Daltons. In one aspect of the invention, the target compound has a molecular weight of about 100, 200, 500, 1000, 2000, 5000, 10,000, 20,000, 50,000, 100,000, 150,000, or 200,000 Daltons. In anther aspect of the invention, the target compound has a weight from about 100 to about 1000 Daltons. In another aspect of the invention, the target compound has a molecular weight from about 100 to about 500 Daltons. In another aspect of the invention, the target compound has a weight from about 500 to about 1000 Daltons. In another aspect of the invention, the target compound has a weight from about 1000 to about 2000 Daltons. In anther aspect of the invention, the target compound has a weight from about 2000 Daltons to about 5000 Daltons. In another aspect of the invention, the target compound has a weight from about 5000 Daltons to about 10,000 Daltons. In another aspect of the invention, the target compound has a molecular weight from about 100 to about 10,000 Daltons. In another aspect of the invention, the target compound has a weight from about 10,000 to about 20,000 Daltons. In another aspect of the invention, the target compound has a weight from about 20,000 to about 50,000 Daltons. In another aspect of the invention, the target compound has a weight from about 50,000 to about 100,000 Daltons. In another aspect of the invention, the target compound has a weight from about 100,000 to about 150,000 Daltons. In another aspect of the invention, the target compound has a weight from about 150,000 to about 200,000

Daltons. In another aspect of the invention, the target compound has a molecular weight from about 10,000 to about 200,000 Daltons.

Databases

One of the many advantages the present invention holds over current NMR crystallography methods is that there are no "throwaway" calculations or experiments. Current methods require expensive NMR calculations for slightly different conformers of the same molecule. When a study is completed, the researcher must discard a host of computed conformers, as they can give no further structural insight. For instance, the study of paclitaxel's structure required the creation, geometry optimization, and the quantum mechanical calculation of NMR shielding for more than 600 separate models. Once these separate models were used to study the structure of paclitaxel, none of these models then had any value for additional different structural examinations. In contrast, the present invention draws from a store of NMR values of known crystal structures. These values may be re-used indefinitely.

This leads to an interesting implication of the present invention, i.e., it will not be necessary to wait for molecule X to begin measuring and cataloguing NMR chemical tensor values for known solids. If one creates a database that contains both the crystal structure and the NMR information of the solid (either measured or calculated), any new structural exploration would have access to the NMR of reference structures for immediate comparison. The automated method of the present invention would then use the experimentally obtained CSPVs to assign molecular conformation in a matter of minutes, rather than the months and years NMR crystallographers currently require for structure prediction of a single solid.

The creation of a database as described above and its corresponding conformational search will produce a general application with immediate value and lasting usefulness in drug development and design. In fact, development may be geared toward solving specific pharmaceutical molecular conformations in the same manner used in Examples 1 and 2. Furthermore, the addition of crystallographic coordinates in ongoing published studies, along with their CSPVs, will serve to enhance the statistical confidence of this technique over time. The utility and applicability of this method cannot be overstated.

Databases can be implemented in any form of hardware storage device (e.g., hard disk, tape storage, etc.) or can be a workstation, computer, cluster of computers, set-top box, or other device having at least one processor. In an embodiment, the database may be located separately from a server. In another non-limiting embodiment, the database may be connected to a wired and/or wireless network that enables a server to communicate with the database across a network.

In one aspect of the invention, the NMR values and atomic coordinates for equivalent atoms within the reference compounds can be obtained from a database. In yet a further aspect, the database is the Cambridge Structural Database.

Example Computer Embodiment

In one aspect of the invention, the methods are automated. In an embodiment of the invention, an apparatus is configured to perform methods for determining the three-dimensional structure of a target compound or methods of screening for test compounds having three-dimensional structures similar to that of a target compound. More specifically, the apparatus comprises a processor and memory, wherein the memory communicates with the processor to carry out methods for determining the three-dimensional structure of a target compound. In a specific embodiment, the methods are performed using well known computer systems. Computer systems can be commercially available and capable of performing the functions described herein, such as computers available from International Business Machines, Apple, Sun, HP, Dell, Compaq, Digital, Cray, etc.

Computer systems include one or more processors (also called central processing units, or CPUs). For example, a computer system can be a workstation, mobile device, computer, cluster of computers, set-top box, or other device having at least one processor. In an embodiment, multiple computer systems may be implemented on the same processing device. Such a processing device may include software, firmware, hardware, or a combination thereof. Software may include one or more applications and an operating system. Hardware can include, but is not limited to, a processor, memory, and/or graphical user interface display. The computing system may also have multiple processors and multiple shared or separate memory components. For example, the computer system may be a clustered computing environment or server farm.

In one aspect of the invention, the identification of reference compounds can be performed by a processor. In another aspect of the invention, the selection of reference compounds can be performed by a processor. One embodiment of the invention is directed to a reference compound identifier for use in methods for determining the three-dimensional structure of a target compound.

In another aspect of the invention, the selection of test compounds can be performed by a processor. One embodiment of the invention is directed to a test compound identifier for use in methods of screening for test compounds having three-dimensional structures similar to that of a target compound.

Computer systems also include a main or primary memory, such as random access memory (RAM). Main memory has stored therein control logic (computer software), and data.

Computer systems also include one or more secondary storage devices. Secondary storage devices include, for example, a hard disk drive and/or a removable storage device or drive, as well as other types of storage devices, such as memory cards and memory sticks. A removable storage drive can be a floppy disk drive, a magnetic tape drive, a compact disk drive, an optical storage device, tape backup, etc.

Removable storage drives interact with removable storage units. Removable storage units include a computer useable or readable storage medium having stored therein computer software (control logic) and/or data. A removable storage unit can be a floppy disk, magnetic tape, compact disk, DVD, optical storage disk, or any other computer data storage device. Removable storage drives read from and/or write to removable storage units in a well known manner.

Computer systems also include input/output/display devices, such as monitors, keyboards, pointing devices, etc., which communicate with communication infrastructure through a display interface. In one aspect of the invention, the generated three-dimensional structure of the target compound is displayed using one or more of the output devices described above.

Computer systems further include a communication or network interface. A communication interface allows the computer system to communicate over a communications path (representing a form of a computer useable or readable medium), such as LAN, WANs, the Internet, etc. A communication interface may interface with remote sites or networks via wired or wireless connections. In one embodiment, the invention is directed to a server configured to obtain NMR values in methods for determining the three-dimensional structure of a target compound or methods of screening for test compounds having three-dimensional structures similar to that of a target compound.

Embodiments of the invention can work with software, hardware, and/or operating system implementations other than those described herein. Any software, hardware, and operating system implementations suitable for performing the functions described herein can be used.

EXAMPLES

The present invention is further defined in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1

Selection of a Test Compound for Structure Determination

Prednisolone tert-butylacetate (PTB) was selected as the test case for the present invention because PTB was the most complex molecule in the 2004 blind crystal structural prediction study conducted by the CCDC. See *Chem. Abstr.* 50:13107C (1956); and Day, G. M. and Motherwell, S., *Acta. Cryst. Sect.* A, A60:s63 (2004). The CCDC has performed multiple blind structural studies in recent years, positing the question: Is it possible to predict the known crystal structure of an organic molecule, given only its chemical diagram? A dozen groups participated in the 1999 study, 17 groups participated in 2001, and 18 groups participated in the structural study of 2004. See Lommerase, J. P. M. et al., *Acta. Cryst. Sect. B,* 56:697-714 (2000); Newsam, J. M. et al., *Curr. Opin. Solid State Mat. Sci.* 4:515-528 (1999); Motherwell, W. D. S., et al., *Acta. Cryst. Sect. B,* 58:647-661 (2002). Yet another blind structural study was conducted in 2007. See Asmadi, A. et al., *J. Phys. Chem. Sect. B.* 113:16303-16313 (2009). A range of methodologies were used to search for and predict the crystal structure, most of which were based on the global minimization of the lattice energy. Particularly large and/or flexible molecules do not submit readily to such a treatment and, unsurprisingly, the structure of PTB with its four ring core and long side chain (shown in FIG. 1) was considered particularly troublesome to constrain. The participants of this study, using high level ab initio methods, were unable to determine the conformation of PTB and some participants of the study concluded that, "it is likely to be some years before such systems can be routinely studied." See Price, S. L., *Adv. Drug Del. Rev.* 56:301-319 (2004).

The spectacular failure of computational methods to accurately and consistently predict the conformation of biomolecular solids does not necessarily imply that there is a corresponding failure in the computational algorithms for energetic minimization. Rather, it speaks to the inherent limitations of using energy methods alone to sort and select molecular conformations. For all but the smallest molecules, there exist a large number of energetically equivalent conformations. It is not possible for energy minimization methods, no matter how sophisticated, to select the actual structure amongst these. Furthermore, the processes of nucleation and crystal growth are not well understood and computational methods are unable to fully account for them. Accordingly, the crystal structure selected by nature may not necessarily be the most thermodynamically favored structure selected by computational means. There is no mechanism in current calculations to account for this apparently random variability in crystallization.

As calculations improve, they might well improve their capability to simultaneously describe conformational and lattice energies. But, because of the limitations cited herein, these improvements will not likely result in the capability of these programs, on their own, to determine the structures of large or flexible pharmaceutically relevant molecules.

PTB was selected to test the accuracy of the present invention for the same reason it was chosen for the CCDC test, i.e., it is a challenging molecule to constrain and characterize. PTB is large and flexible and proved an intractable challenge to the participants of the CCDC blind structural test. As discussed below, the present invention proves sufficiently sensitive and robust to accurately produce the three dimensional crystal structure of PTB. Additionally, as with other steroids whose geometry in the solid state has been related to their biological activity, the reactivity of PTB is linked to its conformation. This feature of PTB makes it even more desirable as a test case.

Example 2 provides a description of how the present invention was applied to find the three-dimensional structure of PTB.

Example 2

NMR Calculations

The following methodology was conducted strictly as a blind structural study, i.e., the coordinates produced by the present invention for PTB were not compared with the reported crystallography coordinates until the study was complete.

Outlined below are the steps used to study PTB using the present invention. Conversions of chemical shielding to chemical shift and calculations for geometry optimizations and NMR values are described as well as methods for comparing the chemical shift principal values (CSPVs) between equivalent nuclei.

The CSPVs for all structures in this study were computed using a well established technique. Using the crystal structure coordinates as published in the Cambridge Structural Database (CSD), the heavy atom dihedral values were fixed and the radial distances and vicinal angles were refined using an AM1 geometry optimization. During this process, the hydrogen atom positions were also refined. From these refined structures, the NMR chemical shift principal values were calculated. All calculations were performed using Gaussian 03 software. See Frisch, M. J. et. al., GAUSSIAN 03 (Revision 0.02), Gaussian, Inc., Wallingford, Conn. (2004). Geometry optimizations were done at an AM1 level of theory and NMR calculations were performed using B3PW91 D95**, yielding the chemical shielding. Shielding values were converted into chemical shift using the values given for sp2 and sp3 carbons by Heider E. M. et al., *Phys. Chem. Chem. Phys.,* 9:6053-6160 (2007).

All shift values were converted into the icosahedral representation as described by Alderman, D. W. et al., *J. Magn. Reson. Ser. A.* 101:188-197 (1993). The icosahedral distance was used according to a previously described procedure to compare the CSPVs from nuclei in calculated structures to analogous nuclei in PTB. See Stueber, D. et al., *J. Chem. Phys.,* 114:9236-9243 (2001); deDios, A. C. and Oldfield, E., Chem. Phys. Lett., 205:108-116 (1993); and deDios, A. C. et al., J. Am. Chem. Soc., 116:7784-7786 (1994).

The CSPVs for PTB were calculated in the same manner described for calculating the NMR values of other crystal structures. The calculated chemical shift values for PTB (named GAJMOT in the Cambridge Structural Database) are given in the icosahedral representation in TABLE 1. Also provided herein is the isotropic chemical shift as predicted by the program Chemdraw, using the 2-dimensional diagram of PTB. This latter method is provided merely as a matter of interest since the Chemdraw technique of estimating chemical shift is not computationally rigorous.

TABLE 1

Computed NMR Shift Values for PTB CSPVs in the Icosahedral Representation

| nuclei | $\chi1 = \chi2 =$ | $\chi3 = \chi4 =$ | $\chi5 = \chi6 =$ | isotropic shift | Chemdraw Shift |
|---|---|---|---|---|---|
| C1 | 235.416 | 119.168 | 101.618 | 152.068 | 155.4 |
| C2 | 183.577 | 95.798 | 86.279 | 121.885 | 128.3 |
| C3 | 242.747 | 163.831 | 121.503 | 176.027 | 185.7 |
| C4 | 166.908 | 92.326 | 90.658 | 116.631 | 124.2 |
| C5 | 249.781 | 144.407 | 93.434 | 162.540 | 168.2 |
| C6 | 39.333 | 28.913 | 29.461 | 32.569 | 32.9 |
| C7 | 44.133 | 33.445 | 29.378 | 35.652 | 32.0 |
| C8 | 33.593 | 28.505 | 24.955 | 29.018 | 29.6 |
| C9 | 63.100 | 52.493 | 53.758 | 56.451 | 59.0 |
| C10 | 52.440 | 37.885 | 27.084 | 39.136 | 39.4 |
| C11 | 83.851 | 68.511 | 51.895 | 68.086 | 66.7 |
| C12 | 48.563 | 37.700 | 37.222 | 41.162 | 39.8 |
| C13 | 60.911 | 42.013 | 40.385 | 47.770 | 44.4 |
| C14 | 66.908 | 44.723 | 44.074 | 51.902 | 49.9 |
| C15 | 37.143 | 18.319 | 16.879 | 24.113 | 20.6 |
| C16 | 55.104 | 35.190 | 23.834 | 38.043 | 29.9 |
| C17 | 94.325 | 82.482 | 84.052 | 86.953 | 89.6 |
| C18 | 27.252 | 17.633 | 15.650 | 20.178 | 14.0 |
| C19 | 31.228 | 21.642 | 17.513 | 23.461 | 25.7 |
| C20 | 273.817 | 205.921 | 142.241 | 207.326 | 211.2 |
| C21 | 92.046 | 70.674 | 50.361 | 71.027 | 65.0 |
| C22 | 230.588 | 133.336 | 152.996 | 172.307 | 173.1 |
| C23 | 57.527 | 40.956 | 36.722 | 45.068 | 48.4 |
| C24 | 30.160 | 26.529 | 23.442 | 26.710 | 31.0 |
| C25 | 47.189 | 28.905 | 17.097 | 31.063 | 29.2 |
| C26 | 48.192 | 33.828 | 14.894 | 32.305 | 29.2 |
| C27 | 38.335 | 27.908 | 13.515 | 26.586 | 29.2 |

All units are in ppm.

Reference Compound Search

Using the methods of the invention, the chemical diagram of PTB was used to determine search parameters for finding reference compounds in a crystallographic database. In order to show how this search was conducted, the following example of a single search parameter is provided, using the substructure drawn for C1 as the target nuclei.

In order to search the CSD for structures that share the local stereochemistry of PTB in the region surrounding the target atom (in this case, the C1 position), the C1 substructure was created by drawing segments of PTB out to three bond lengths from C1. As the fourth underlying concept underlying the invention is that structural features beyond this three bond length distance generally possess limited influence on the chemical shift, nuclei may therefore be discarded from the substructure model without losing accuracy in the calculated CSPV value of the target nuclei. FIG. 2 illustrates this concept using ovals and boxes to indicate the atoms with primary, secondary and tertiary influence on the C1 CSPVs. The atoms enclosed by single-lined ovals indicates those positions expected to have primary influence on the nuclear spin of the C1 atom ($\alpha$ position). Boxed atoms indicate features of secondary influence ($\beta$ position), and the double-lined ovals indicates tertiary influence ($\gamma$ position) on C1.

Because the types of atoms adjacent to target nuclei and the spatial relationships between them are of interest, it then becomes useful to think of atomic bonds as rotation axes. This allows one to have a uniform description of the requirements for the substructure search parameters; the boxed and circled rotation axes must be described by a complete set of dihedral parameters.

In order to make this possible, the search parameters laid out in the C1 substructure retained "descriptors," defined as atoms that allow the axis formed by the bonds either circled by single-lined ovals, boxes, or double-lined ovals, to serve as rotation axes in the descriptions of the dihedral. For instance, the bond formed by C6-C5 may serve as a rotation axis only if the C7 position is retained to define the dihedral C7-C6-C5=C10 or C7-C6-C5=C4. In this case, C7 is called a descriptor.

The C1 substructure shown in FIG. 2 was entered as the search criteria in the CSD (with correct valences assigned).

As shown in FIG. 2, the positions of the atoms immediately adjacent to C1 (e.g., the $\alpha$ position) will have the most influence on the chemical shift of C1 (C1=C2 and C10-C1). The dihedral values centering on these rotation axes are referred to as the "primary dihedral" values in the C1 substructure. These positions can be completely characterized by defining the four angles C3-C2=C1-C10, C5-C10-C1=C2, C9-C10-C1=C2, and C10-ipso-C10-C1=C2. It is clear then that the C1 position has four primary degrees of freedom. This allows one to formalize a treatment to compare conformational differences between reference compounds and PTB. The "average angular difference" would then be the sum of the differences between the primary angles of the reference compound and PTB, divided by the number of primary degrees of freedom. The number of primary degrees of freedom for every target atomic position is given in Table 2.

TABLE 2

Number of Substructures Matching the Target Nuclei Search Criteria (i.e., out to the third bond length)

| Target Nuclei | Number of CSD molecules (reference compounds) matching the target nuclei substructure and used to study local conformation | Number of primary angles from this nuclear location (degrees of freedom) |
|---|---|---|
| C1 | 23 | 4 |
| C2 | 23 | 3 |
| C3 | 27 | 3 |
| C4 | 26 | 4 |
| C5 | 22 | 4 |
| C6 | 43 | 3 |
| C7 | 39 | 3 |
| C8 | 26 | 9 |
| C9 | 14 | 11 |
| C10 | 13 | 11 |
| C11 | 26 | 7 |
| C12 | 21 | 5 |
| C13 | 18 | 15 |
| C14 | 25 | 8 |
| C15 | 26 | 3 |
| C16 | 24 | 4 |
| C17 | 24 | 8 |
| C18 | 32 | 4 |
| C19 | 20 | 4 |
| C20 | 16 | 5 |
| C21 | 14 | 3 |
| C22 | 15 | 4 |
| C23 | 14 | 2 |
| C24 | 5 | 1 |

Also listed in TABLE 2 are the number of degrees of freedom used to completely characterize the target nuclei. This number is higher for those nuclei bonded to three or more heavy atoms. These nuclei serve as intersections in the molecule.

One does not need to specify a directional preference for the $CH_3$ group at the C10 position, but instead requires that the database search selects reference compounds with both a stereo-up and a stereo-down bond. This approach was intentional, because it was meant to test whether the methods of invention would be able to select between two such structures to determine the actual form of the PTB moiety.

Twenty-seven structures (referred to herein as reference compounds) containing this fragment of the C1 substructure were collected from the CSD (in the form of a CIF file). Of the twenty-seven reference compounds, some were discarded as impractical for the purposes of this study; molecules with heavy atoms just beyond the three-bond-length limit were excluded because the heavy atom would unduly influence the chemical shift. While charged molecules were also removed from the list of reference compounds for the same reason, the methods of the invention can also be used to determine the three-dimensional structure of charged molecules.

Examples of the reference compounds extracted from the CCDC database are displayed in FIG. 3. FIG. 3 displays thirteen reference compounds that share the C1 substructure given in FIG. 2. Of the 27 carbon nuclei in PTB, 24 are likely to exhibit sensitivity to structure. Symmetry arguments for C25, C26 and C27 allow one to remove these positions from consideration. 24 substructures were modeled to simulate the local environment of each target nuclear position. This was done in the same manner as was just outlined for C1. The number of crystallographic structures matching the criteria for each nuclear position is given in Table 2.

For those target nuclei whose substructures yielded far fewer matches in the CSD, the chance of a correct geometry match is also diminished. For instance, the 39 reference compounds for the substructure of the C7 position provide a better opportunity for finding a CSPV match to PTB at this position than the 14 reference compounds found for the substructure surrounding C21. In the case of insufficient available reference compounds, the structural information from next-door-neighbor nuclei may be used, as the two target nuclei will share a primary dihedral angle.

Results and Discussion

At each target nuclear position, the root mean square (rms) distance is calculated between the reference compound CSPVs and the CSPVs of PTB. An F-test is then used to sort the reference compounds according to the goodness of the CSPV match. F-values for each predicted structure were obtained as $F=(d_i/d)^2$ where $d_i$ represents the rms icosahedral distance of the $i^{th}$ reference compound from PTB, and d represents the model in the set that most closely matched the NMR data from PTB. In the instance where d was exceptionally small (i.e. less than 1), the value of d=1.2 was used. Where the F-test could not eliminate the reference compound with at least 85% confidence, the reference compound was retained. At several nuclear positions, this method readily removed reference compounds with CSPVs that did not coincide with those of PTB, leaving only a small number of reference compounds with a good CSPV match.

Most often, the similarity in CSPVs of the retained reference compounds for a particular target nuclei was the natural result of local conformational similarity. In other instances, the target nuclear CSPV was simply less sensitive to conformation (e.g. if the first order effects of stereochemistry dominate the shift). This effect can be observed where the range of conformational differences in the reference compounds does not correspond to a similar range of differences in CSPV root mean square (rms) distances at the target position. These effects are shown in TABLE 3, where the range of differences in the primary dihedral angle between the reference compounds with respect to PTB are listed.

For each of the target nuclear positions, the average difference between the primary angles of PTB and analogous primary angles of the reference compounds is listed. Also listed is the range of CSPV fits between the reference compounds and PTB (in parts per million). The name of the reference compound selected by the methods of the invention are also listed to represent the local geometry surrounding the nuclear position. In the fourth column, the selected reference compound and its average angular difference (in the primary dihedrals) from PTB are listed.

TABLE 3

| Target nuclei | Range (in degrees) of average angular difference between all reference compounds and PTB | Range (in ppm) of rms distance between reference compounds and PTB | Reference compound with CSPV match at this nuclear position | Average angular difference of selected reference compound with PTB (in degrees) |
|---|---|---|---|---|
| C1 | 1.969-167.451 | 0.554-4.110 | VIFSOS | 2.486 |
| C2 | 1.427-32.837 | 0.194-3.273 | RHBUXP10 | 2.603 |
| C3 | 0.988-103.440 | 0.097-3.334 | BAXSAU | 3.944 |
| C4 | 0.944-7.992 | 0.208-6.801 | HXPRED | 1.802 |
| C5 | 1.325-208.214 | 0.853-6.086 | DABJAR | 2.947 |
| C6 | 1.073-169.740 | 0.208-3.062 | VIFSOS | 2.703 |
| C7 | 0.795-164.776 | 0.216-7.393 | FAJWAO | 1.948 |
| C8 | 2.001-83.627 | 0.557-8.466 | HXPRED | 2.001 |
| C9 | 2.296-90.964 | 0.882-9.231 | DABJAR | 2.296 |
| C10 | 2.761-8.753 | 0.185-2.632 | RHBUXP10 | 8.753 |
| C11 | 4.282-143.790 | 0.5084-4.470 | MTHPRG | 7.688 |
| C12 | 1.266-52.085 | 0.2684-9.065 | FEHLAF | 3.178 |
| C13 | 1.353-7.833 | 0.498-7.589 | FEHKIM | 1.353 |
| C14 | 1.360-198.767 | 0.925-21.257 | VIFSOS | 2.470 |
| C15 | 0.943-192.793 | 0.192-23.480 | GAJMEJ | 6.131 |
| C16 | 0.488-174.242 | 0.463-5.326 | FEHKIM | 0.488 |
| C17 | 1.178-253.475 | 0.269-63.896 | FEHKIM | 1.265 |
| C18 | 1.551-138.856 | 0.529-11.074 | RESVEQ | 2.876 |
| C19 | 0.564-160.229 | 1.240-21.441 | SHBUXP10 | 3.339 |
| C20 | 1.968-164.071 | 0.858-194.402 | FEHLAF | 3.376 |
| C21 | 1.535-96.781 | 0.439-138.724 | GAJLUY | 1.536 |
| C22 | 12.994-130.093 | 1.159-6.373 | GIBBNC | 12.994 |
| C23 | 1.927-155.355 | 1.410-11.260 | BIJTAP | 28.180 |
| C24 | 19.954-109.885 | 0.628-1.276 | GAJMEJ | 13.510 |

Column 3 then lists the range of differences between the CSPVs of the target nuclei of these reference compounds with respect to PTB. For instance, the CSPVs at the C6 position did not appear to be sensitive to conformational differences (the average angular difference between the reference compounds varied by almost 180 degrees), although the range of rms distances between the C6 CSPVs had a maximum value of 3.062 ppm. In contrast, the C5 position appeared to be more sensitive to structural differences (angular difference 1.325–208.214 degrees, rms distance 0.853–6.086 ppm). The C9 position appeared to be similarly sensitive (angular difference 2.296–90.964 degrees, rms distance 0.882–9.231).

It was observed that the CSPVs of nuclei located at an intersection provide extremely useful structural information. These intersection points have the highest numbers of degrees of freedom and, therefore, the largest amount of structural variation. The evidence provided by intersection nuclei give the widest range of values and, therefore, the largest number of throwaway answers. In future studies, these locations can be used as guideposts for determining structure.

In the case where the retained reference compound structures shared similar conformations at their primary, secondary, and tertiary positions, a single reference compound among these was selected to represent the preferred conformation of the group. This was done by arbitrarily selecting the structure with the "best" CSPV match, even if this match was statistically no better than that of the other retained structures. If the retained reference compounds had different conformations from one another at these positions (as was described for the reference compounds retained at the C6 nuclear position), the data of next-door-neighbor target nuclei was used to test the veracity of each retained reference compound conformation. For instance, the rotation axis of C5-C6 is the centerpiece of a "primary dihedral" for both the C5 and C6 target nuclei. The sensitive CSPVs at the C5 position can then be used to verify the information given by the C6 substructure search. By combining independent information from each nuclear location, this method self-checks for aberrant results, eliminating outliers from the set.

When reference compounds had been selected to represent the best CSPV matches for each target nuclei (listed in TABLE 3), the primary dihedral angles for each target nuclear position were identified. Because next-door-neighbor target nuclei share a primary dihedral angle rotation axis, the retained dihedral values of nuclei with appropriately sensitive CSPVs were averaged. By merging the conformations of various moieties from multiple reference compounds, and refining vicinal angles and radial distances, a three-dimensional structure for PTB was generated. The resultant structure is a mosaic image, constructed from independent CSPV information at each nuclear location.

To ascertain the accuracy of the methods of the invention, the generated three-dimensional structure of PTB was compared with the published crystal structure of PTB (GAJMOT). The results of this comparison are shown in TABLE 3. Here, for each target nuclei examined, the range of angular fit between the primary dihedral values of all reference compounds and those of PTB is listed. Similarly, the rms distances (in ppm) between the CSPVs of all reference compounds and the CSPVs of PTB are also listed. This allows one to see the variety of values that the methods of the invention could select among at each target nuclei position, making it clear that the success of this method does not result from a lack of conformational options.

In most instances, the range of possible values includes an extrema of more than 100° (an angular difference of 180° may indicate that the reference compound structure is an enantiomer of PTB). In the fifth column of TABLE 3, the average angular difference between the primary angles for the selected reference compound structure and the same angles of PTB are listed.

For most (21 of 24) target nuclear positions, the average angular value is no more than 7° different from analogous angles in PTB, indicating a high degree of accuracy. The greatest angular deviation is only 28.2° and this result is likely due to the relatively small number of reference compounds available for comparison at the C23 position (see TABLE 2). This result illustrates an important aspect of the claimed invention: the accuracy of the method improves as additional reference compounds are included in the search. Researchers may therefore improve structural prediction for a particularly difficult molecule by performing crystallization studies on molecules possessing the moieties of interest.

The generated three-dimensional structure of PTB is of especially high quality, deviating from the known crystal structure of PTB by an all atom root-mean-square-deviation (rmsd) of only 0.081. To showcase the similarities in structure that are listed in TABLE 2, an overlay of the generated three-dimensional structure of PTB and GAJMOT is illustrated in FIG. 4.

In FIG. 4, it is clear that there is a high degree of agreement in the four ring core. It is particularly worthy that the methods of the invention differentiated between the stereo-up and stereo-down bond options of the $CH_3$ group at the C10 position. Clearly, the end of the sidechain is the only area that varies from the crystal structure, and the variation is minimal.

Summary and Conclusions

In this Example, the methods of the invention were employed to determine the three-dimensional structure of PTB. First, a series of substructures was constructed to represent the local environment of each carbon nuclei in the molecule. Then, these substructures were used as search criteria in the Cambridge Structural Database to find reference compounds with identical local stereochemistry yet varying conformations. Then, the CSPVs of the reference compounds were compared with the CSPVs of PTB and reference compounds with poor CSPV matches were eliminated. Finally, using the retained reference compound structures, a composite three-dimensional structure of PTB was generated.

The application of this method gave insight into its strengths, and demonstrates how the method may be applied to multiple molecules in a widescale fashion.

One of the greatest strengths of the methods of the invention is that they use independent information from many nuclear positions. By comparing shift values between multiple nuclear positions, the methods self-check against anomalous results at any given location. This is a unique feature of the invention and makes the methods particularly robust.

Another useful facet of the methods outlined above emerged during this study. That is, the methods can re-use reference compounds between one step and the next. In other words, a reference compound may possess enough structural features to characterize multiple target nuclei according to the parameters that have been laid out. This phenomenon occurred frequently during the study of PTB, reducing the total number of reference compounds needed to obtain the structure of PTB (listed in TABLE 2) from 500 to 80. Furthermore, the 80 structures that were used to study PTB may be included in the NMR/coordinate database and re-used in future studies.

This result is particularly surprising when contrasted against other NMR crystallography methods. The computational models created and used in other methods lose their value upon completion of the study. For instance, the structure of paclitaxel required the manual formulation of over 600 separate models, none of which could be re-used in future structural examinations. This feature of the invention will prove useful in reducing the computational cost of future structural studies.

The structure discovered using the invention showed remarkable similarity with the reported crystal structure of PTB. This successful prediction indicates that these methods may be used to accurately determine the conformation of other biomolecules.

Example 3

Screening Test Compounds

The following methodology can be used in rational drug design, i.e., identify test compounds that have similar three-dimensional structures as a target compound known to have therapeutic properties.

As mentioned above, conversions of chemical shielding to chemical shift and calculations for geometry optimizations and NMR values are described as well as methods for comparing the chemical shift principal values (CSPVs) between equivalent nuclei.

The CSPVs for all test compound structures in this study can be computed using well established techniques. One may use the crystal structure coordinates as published in the Cambridge Structural Database for the test compounds, whereby the heavy atom dihedral values can be fixed and the radial distances and vicinal angles can be refined using an AM1 geometry optimization. During this process, the hydrogen atom positions can also be refined. From these refined structures, the NMR chemical shift principal values can be calculated. Calculations can be performed using. Gaussian 03 software. Geometry optimizations can be done at an AM1 level of theory and NMR calculations can be performed using B3PW91 D95**, yielding the chemical shielding. Shielding values can be converted into chemical shift using the values given for sp2 and sp3 carbons as described above.

Shift values can be converted into the icosahedral representation as described by Alderman, D. W. et al., *J. Magn. Reson. Ser. A*. 101:188-197 (1993). The icosahedral distance can be used according to a previously described procedure to compare the CSPVs from nuclei in calculated test compound structures to analogous nuclei in the target compound.

Alternatively, the CSPVs for test compounds can be calculated from experimentally derived NMR measurements.

The CSPVs for the target compound can either be calculated in the same manner described for calculating the NMR values of other crystal structures or from experimentally derived NMR measurements. The calculated chemical shift values for the target compound can be given in icosahedral representation.

Using the methods of the invention, the chemical diagram of the target compound can be used to identify test compounds having similar substructures. Substructures can be generated by drawing segments of the target compound out to three bond lengths from individual target compound atoms. Just as substructures for the heavy atoms at C1-C24 in PTB were generated in Example 2 to identify reference compounds having similar two-dimensional structures as PTB, so too can the substructures of a target compound be used to initially identify those test compounds having similar two-dimensional structures as the target compound.

At each target nuclear position, the root mean square (rms) distance can be calculated between the test compound CSPVs and the CSPVs of the target compound. An F-test can then used to sort the test compounds according to the goodness of the CSPV match. F-values for each predicted structure can be obtained as $F=(d_i/d)^2$ where $d_i$ represents the rms icosahedral distance of the $i^{th}$ test compound from the target compound, and d represents the model in the set that most closely matched the NMR data from the target compound. In the instance where d is exceptionally small (i.e. less than 1), the value of d=1.2 can be used. Where the F-test can not eliminate the test compound with at least 85% confidence, the test compound will be retained.

Similarly, global rms distances can be calculated taking into consideration the CSPVs of all target nuclei in test compounds and the CSPVs of all target nuclei in the target compound. Test compounds having the lowest global rms distance values will be selected for further testing, i.e., biological, chemical, etc.

The test compounds identified using the invention will have three-dimensional structures similar to the crystal structure of the target compound. Accordingly, the identified test compounds will be better suited to bind biological targets because of their similar crystal structure.

CONCLUSION

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor, and thus, are not intended to limit the present invention and the appended claims in any way.

The invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general scope of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology and phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for determining the three-dimensional structure of a target compound by nuclear magnetic resonance (NMR) crystallography, said method comprising:
   (a) identifying a set of reference compounds from existing molecules which have known three-dimensional structure and which comprise similar substructures present in said target compound;
   (b) obtaining NMR values for said target compound and both NMR values and atomic coordinates for equivalent atoms within said reference compounds;
   (c) selecting a subset of reference compounds based upon the most suitable calculated relevant statistical match (rsm) for equivalent atoms in each reference compound identified in (a); and
   (d) obtaining and compiling the atomic coordinate data for equivalent atoms of reference compounds selected in (c) to generate a three-dimensional structure of said target compound.

2. A method for determining the three-dimensional structure of a target compound by NMR Crystallography, said method comprising:
   (a) generating substructures of said target compound;
   (b) identifying a set of reference compounds from existing molecules which have known three-dimensional structure and which comprise the identical substructures generated in (a);
   (c) obtaining NMR values for said target compound and both NMR values and atomic coordinates for reference compounds;

(d) calculating root mean square (rms) values for equivalent heavy atoms in each reference compound identified in (b);

(e) selecting from the reference compounds identified in (b), a subset of reference compounds having the lowest calculated rms values; and (f) obtaining and compiling the atomic coordinate data for the equivalent heavy atoms of the reference compounds selected in (e) to generate a three-dimensional structure of said target compound.

3. The method of claim 1 or 2, wherein the NMR values of reference compounds are obtained by experimental measurement.

4. The method of claim 1 or 2, wherein the NMR values and atomic coordinates for equivalent atoms within said reference compounds are obtained from a database.

5. The method of claim 1 or 2, wherein said generated three-dimensional structure of said target compound is displayed.

6. A method of screening for reference compounds having three-dimensional structures similar to that of a target compound, said method comprising:

(a) providing two-dimensional drawings of said reference compounds, NMR values of a preselected nuclear species contained within said reference compounds, NMR values of the same preselected nuclear species for said target compound, and atomic coordinate data for said target compound;

(b) selecting a first atom of said target compound;

(c) generating a substructure of said target compound that includes all other atoms within said target compound that are separated by no more than 3 chemical bonds from said heavy atom;

(d) identifying a set of reference compounds comprising substructures similar to the target compound substructure generated in (c);

(e) calculating relevant statistical match (rsm) values for each of the reference compounds identified in (d);

(f) selecting from the reference compounds identified in (d), a subset of the reference compound having the most suitable calculated rsm value;

(g) repeating (c)-(f) for each of the remaining atoms of said target compound;

(h) calculating global rsm values for each of the reference compounds selected in (f); and (i) selecting from the reference compounds identified in (f), the reference compound having the lowest calculated global rsm value.

7. The method of claim 6, wherein the NMR values of reference compounds in (d) are obtained by experimental measurement.

8. The method according to claim 1 or 6, wherein said NMR values are calculated or measured, or both calculated and measured, for one or more of the following types of interactions: Zeeman interactions, quadrupolar interactions, dipolar couplings, paramagnetic interactions, chemical shift, chemical shielding, and J-couplings.

9. The method of claim 1, further comprising calculating chemical shifts and chemical shielding for said generated three-dimensional structure and comparing the calculated chemical shifts and calculated chemical shielding to the chemical shifts and chemical shielding obtained by experimental measurement for said target compound.

10. The method according to claim 1, further comprising refining said generated three-dimensional structure based on measurements obtained for said target compound by one or more of the following techniques: x-ray diffraction, neutron diffraction and electron diffraction.

11. The method according to claim 1 or 6, wherein the NMR values are obtained from a nuclear species in said target compound that is selected from the group consisting of: $^{13}C$, $^{15}N$, $^{17}O$, and $^{31}P$.

12. An apparatus configured to perform the methods of claim 1, wherein the apparatus comprises a processor and memory.

13. A method for identifying reference compounds associated with a given target compound for use in a method for determining the three-dimensional structure of a target compound by nuclear magnetic resonance (NMR) crystallography, said method comprising:

(a) identifying, using a processor, a set of reference compounds from existing molecules which have known three-dimensional structure and which comprise similar substructures present in said target compound;

(b) obtaining NMR values for said target compound and both NMR values and atomic coordinates for equivalent atoms within said reference compounds;

(c) selecting a subset of reference compounds based upon the most suitable calculated relevant statistical match (rsm) for equivalent atoms in each reference compound identified in (a); and (d) obtaining and compiling the atomic coordinate data for equivalent atoms of reference compounds selected in (c) to generate a three-dimensional structure of said target compound.

14. A system for obtaining nuclear magnetic resonance (NMR) values that determines the three-dimensional structure of a target compound by NMR crystallography, comprising:

a database stored in memory and configured to execute on a processor and further configured to:

(a) identify a set of reference compounds from existing molecules which have known three-dimensional structure and which comprise similar substructures present in said target compound;

(b) obtain NMR values for said target compound and both NMR values and atomic coordinates for equivalent atoms within said reference compounds;

(c) select a subset of reference compounds based upon the most suitable calculated relevant statistical match (rsm) for equivalent atoms in each reference compound identified in (a); and (d) obtain and compile the atomic coordinate data for equivalent atoms of reference compounds selected in (c) to generate a three-dimensional structure of said target compound.

* * * * *